(12) United States Patent
King et al.

(10) Patent No.: US 7,049,314 B2
(45) Date of Patent: May 23, 2006

(54) CYCLOPENTYL INDOLE DERIVATIVES

(75) Inventors: Dalton King, Hamden, CT (US); Jeffrey A. Deskus, Marlborough, CT (US); John E. Macor, Guilford, CT (US); Ronald J. Mattson, Meriden, CT (US); Zhaoxing Meng, Middletown, CT (US); Charles P. Sloan, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 284 days.

(21) Appl. No.: 10/662,745

(22) Filed: Sep. 15, 2003

(65) Prior Publication Data

US 2004/0077705 A1    Apr. 22, 2004

Related U.S. Application Data

(60) Provisional application No. 60/411,733, filed on Sep. 18, 2002.

(51) Int. Cl.
- A61K 31/535    (2006.01)
- A61K 31/445    (2006.01)
- A61K 31/40     (2006.01)
- C07D 413/06    (2006.01)
- C07D 209/04    (2006.01)

(52) U.S. Cl. .............. 514/235.12; 514/323; 514/414; 544/143; 546/201; 548/455; 548/465

(58) Field of Classification Search ............. 548/465, 548/455; 546/201; 544/143; 514/414, 235.2, 514/323
See application file for complete search history.

(56) References Cited

U.S. PATENT DOCUMENTS

| 5,468,767 | A | 11/1995 | Cipollina et al. |
| 5,468,768 | A | 11/1995 | Cipollina et al. |
| 5,583,149 | A | 12/1996 | Cipollina et al. |
| 5,607,961 | A | 3/1997 | Cipollina et al. |
| 2004/0063768 | A1* | 4/2004 | Denhart et al. ............ 514/394 |

FOREIGN PATENT DOCUMENTS

WO    WO 02/079152 A1    10/2002

OTHER PUBLICATIONS

Fuller, "Pharmacologic Modification of Serotonergic Function: Drugs for the Study and Treatment of Psychiatric and Other Disorders," J. Clin. Psychiatry, 47:4 (Suppl.), Apr. 1986, pp. 4-8.

Kim, et al., "Short-Term Analysis of the Effects of As Needed Use of Sertraline at 5 p.m. for the Treatment of Premature Ejaculation," Urology, 54 (3), 1999, pp. 544-547.

McMahon, et al., "Treatment of Premature Ejaculation with Paroxetine Hydrochloride As Needed: 2 Single-Blind Placebo Controlled Crossover Studies," J. of Urology, 161, Jun. 1999, pp. 1826-1830.

Haensel, et al., "Clomipramine and Sexual Function with Men in Premature Ejaculation and Controls," J. of Urology, 156, Oct. 1996, pp. 1310-1315.

McMahon, et al., "Treatment of Premature Ejaculation with Paroxetine Hydrochloride," International Journal of Impotence Research, 11, 1999, pp. 241-246.

* cited by examiner

Primary Examiner—Johann Richter
Assistant Examiner—Ebenezer Sackey
(74) Attorney, Agent, or Firm—James Epperson; Shah R. Makujina

(57) ABSTRACT

The present invention relates to compounds of Formula (I) and pharmaceutically acceptable salts or solvates thereof and pharmaceutically acceptable formulations comprising said compounds

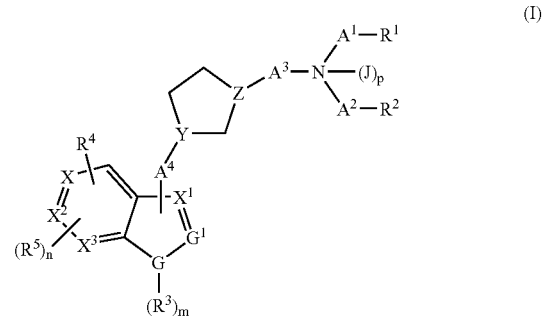

useful for the treatment of premature ejaculation, depression, attention deficit hyperactivity disorder, obsessive-compulsive disorder, post-traumatic stress disorder and substance abuse disorders.

48 Claims, No Drawings

CYCLOPENTYL INDOLE DERIVATIVES

CROSS REFERENCE TO RELATED APPLICATION

This non-provisional application claims priority from provisional application U.S. Ser. No. 60/411,733 filed Sep. 18, 2002.

FIELD OF THE INVENTION

The present invention relates to cyclopentylindole derivatives and pharmaceutical compositions comprising said derivatives useful for the treatment of various psychiatric disorders and premature ejaculation.

BACKGROUND OF THE INVENTION

Selective serotonin reuptake inhibitors (SSRIs) are effective for the treatment of mental depression and have been reported to be useful for treating chronic pain. See R. W. Fuller, "Pharmacologic Modification of Serotonergic Function: Drugs for the Study and Treatment of Psychiatric and Other Disorders," *J. Clin. Psychiatry*, 47:4 (Suppl.) April 1986, pp. 4–8 and Selective Serotonin Reuptake Inhibitors. Edited by J P Feighner and W F Boyer, Chichester, England. John Wiley & Sons, 1991, pp 89–108. SSRI's have also demonstrated efficacy for the treatment of anxiety disorders. More recently, SSRI's have demonstrated efficacy in the treatment of premature ejaculation. See Kim and Paick, Short-term Analysis of the Effects of As Needed Use of Sertraline at 5 pm for the Treatment of Premature Ejaculation, *Urology* 54:544–547 (1999); Kim and Paick, Self Therapy with Sertraline given PRN at 5 pm in treatment of Premature Ejaculation, *Journal of Urology* 54:544–547 (1998); McMahon and Touma, Treatment of Premature Ejaculation with Paroxetine Hydrochloride As Needed: 2 Single-Blind Placebo Controlled Crossover Studies *Journal of Urology* 161:1826–1830 (1999); Haensal et al., Clomipramine and sexual function in men with premature ejaculation and controls *Journal of Urology* 158:1310–1315 (1998); and McMahon and Touma, Treatment of Premature Ejaculation with Paraoxetine Hydrochloride *International Journal Impotence Research* 11:241–246 (1999).

In U.S. Pat. No. 5,468,768, $C_{5-7}$cycloalkyl indole derivatives, more particularly examples of substituted indol-3yl cyclohexyl amines were disclosed for the treatment of headache. See also U.S. Pat. No. 5,583,149. In U.S. Pat. No. 5,468,767 $C_{5-7}$cycloalkyl indole derivatives, more particularly examples of substituted indol-3yl cyclohexyl amines were disclosed for the treatment of depression. See also U.S. Pat. No. 5,607,961. None of said patents discloses use of said derivatives for the treatment of premature ejaculation. Thus, novel SSRI's effective for the treatment of premature ejaculation and other disorders would be greatly advantageous.

SUMMARY OF THE INVENTION

Thus according to a first embodiment of a first aspect of the present invention are provided compounds of Formula (I)

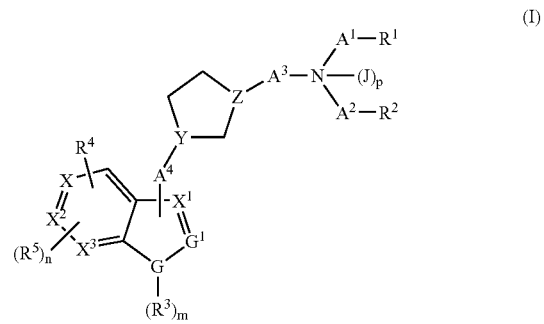

and pharmaceutically acceptable salts or solvates thereof
wherein
$A^1$ and $A^2$ are each independently $C_{1-4}$alkylene or a bond;
$A^3$ is a bond, $C_{1-4}$alkylene or $C_{1-4}$alkylidene;
$A^4$ is $C_{1-4}$alkylene or a bond and is attached to X, $X^1$ or $X^2$;
X, $X^1$, $X^2$ and $X^3$ are independently C or CH;
J is $C_{1-4}$alkyl;
p is 0 or 1;
$R^1$ and $R^2$ are independently H, $C_{1-3}$alkyl, $C_{3-6}$cycloalkyl, phenyl, —O-phenyl, —N(H)C(O)O—$C_{1-4}$alkyl or $C_{1-4}$alkyl-N(H)C(O)O—;
  said $C_{3-6}$cycloalkyl, phenyl or O-phenyl being independently and optionally substituted with $C_{1-4}$alkyl, $C_{1-3}$alkoxy, indolyl or halo;
    wherein said indolyl is optionally substituted by halo or cyano;
  or are independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano;
  or wherein -$A^1$-$R^1$ and -$A^2$-$R^2$ together with the nitrogen to which they are attached form pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, indolyl, isoindolyl, indolinyl, isoindolinyl, quinolinyl, dihydroquinolinyl, tetrahydroquinolinyl, isoquinolinyl, dihydroisoquinolinyl or tetrahydroisoquinolinyl and are optionally substituted with halo, $C_{1-4}$alkyl, $C_{1-4}$alkoxy, cyano or benzyl;
$R^3$ is H or $C_{1-4}$alkyl;
m is 0 or 1;
$R^4$ and $R^5$ are independently hydrogen, cyano, halo, nitro, $C_{1-3}$alkyl or $C_{1-3}$perfluoroalkyl;
  wherein said $R^4$ or $R^5$ may be independently attached to $G^1$, X, $X^1$, $X^2$ or $X^3$;
n is 0 or 1;
G is N, O or S;
$G^1$ is N, C or CH;
Y is (D)H wherein D is C; and
Z is (E)H wherein E is C;
provided that
  both $R^4$ and $R^5$ are not attached to the same of said $G^1$, X, $X^1$, $X^2$ or $X^3$;

if G is or S, then m is 0;
if G is N, then m is 1;
if $R^1$ is $C_{3-6}$cycloalkyl, phenyl or O-phenyl being independently and optionally substituted with $C_{1-4}$alkyl, $C_{1-3}$alkoxy, indolyl or halo; wherein said indolyl is optionally substituted by halo or cyano, then $R_2$ is H or $C_{1-3}$alkyl;
if $R_2$ is $C_{3-6}$cycloalkyl, phenyl or O-phenyl being independently and optionally substituted with $C_{1-4}$alkyl, $C_{1-3}$alkoxy, indolyl or halo; wherein said indolyl is optionally substituted by halo or cyano, then $R_1$ is H or $C_{1-3}$alkyl;
if $-A^1-R^1$ and $-A^2-R^2$ together with the nitrogen to which they are attached form pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, indolyl, isoindolyl, indolinyl, isoindolinyl, quinolinyl, dihydroquinolinyl, tetrahydroquinolinyl, isoquinolinyl, dihydroisoquinolinyl or tetrahydroisoquinolinyl and are optionally substituted with halo, $C_{1-4}$alkyl, $C_{1-4}$alkoxy, cyano or benzyl, then p is 0;
if $R^1$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^1$, then $A^1$ is $C_{2-4}$alkylene;
if $R^2$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^2$, then $A^2$ is $C_{2-4}$alkylene;
if $R^1$ is N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^2$ is H or $C_{1-3}$alkyl;
if $R^2$ is —N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl,
wherein said heterocyclic moieties are optionally substituted with halo, $C_{1-4}$alkyl, $C_{1-4}$alkoxy or cyano, then $R^1$ is H or $C_{1-3}$alkyl;
if $R^4$ or $R^5$ are attached to $G^1$, then $G^1$ is C;
if $A^4$, $R^4$ or $R^5$ are attached to X, then X is C;
if $A^4$, $R^4$ or $R^5$ are attached to $X^1$, then $X^1$ is C;
if $A^4$, $R^4$ or $R^5$ are attached to $X^2$, then $X^2$ is C;
if $R^4$ or $R^5$ are attached to $X^3$, then $X^3$ is C.

According to another embodiment of the first aspect of the present invention are provided compounds of Formula (I) according to the first embodiment of the first aspect wherein p is 0.

According to another embodiment of the first aspect of the present invention are provided compounds of Formula (I) according to the first embodiment of the first aspect wherein G is N and $G^1$ is CH.

According to another embodiment of the first aspect of the present invention are provided compounds of Formula (I) according to the first embodiment of the first aspect wherein G is S and $G^1$ is CH.

According to another embodiment of the first aspect of the present invention are provided compounds of Formula (I) according to the first embodiment of the first aspect wherein G is N and $G^1$ is N.

According to another embodiment of the first aspect of the present invention are provided compounds of Formula (I) according to the first embodiment of the first aspect wherein G is S and $G^1$ is N.

According to another embodiment of the first aspect of the present invention are provided compounds of Formula (I) according to the first embodiment of the first aspect wherein G is O and $G^1$ is N.

According to another embodiment of the first aspect of the present invention are provided compounds of Formula (I) according to the first embodiment of the first aspect wherein $R^1$ is methyl and $R^2$ is methyl.

According to another embodiment of the first aspect of the present invention are provided compounds of Formula (I) according to the first embodiment of the first aspect wherein $R^1$ is H and $R^2$ is $C_{3-6}$cycloalkyl wherein said $C_{3-6}$cycloalkyl is substituted with indolyl and wherein said indolyl is optionally substituted by halo or cyano.

According to another embodiment of the first aspect of the present invention are provided compounds of Formula (I) according to the first embodiment of the first aspect wherein $A^1$ is a bond, $R^1$ is methyl, $A^2$ is a bond and $R^2$ is methyl.

According to another embodiment of the first aspect of the present invention are provided compounds of Formula (I) according to the first embodiment of the first aspect wherein $R^1$ and $R^2$ are independently H, $C_{1-3}$alkyl, $C_{3-6}$cycloalkyl, phenyl, —O-phenyl, —N(H)C(O)O—$C_{1-4}$alkyl or $C_{1-4}$alkyl-N(H)C(O)O—; said $C_{3-6}$cycloalkyl, phenyl or O-phenyl being independently and optionally substituted with $C_{1-4}$alkyl, $C_{1-3}$alkoxy or halo.

According to another embodiment of the first aspect of the present invention are provided compounds of Formula (I) according to the first embodiment of the first aspect wherein $R^1$ and $R^2$ are independently H, $C_{1-3}$alkyl, phenyl, said phenyl being independently and optionally substituted with $C_{1-4}$alkyl, $C_{1-3}$alkoxy or halo.

According to another embodiment of the first aspect of the present invention are provided compounds of Formula (I) according to the first embodiment of the first aspect wherein $R^1$ and $R^2$ are independently H or unsubstituted $C_{1-3}$alkyl or phenyl.

According to another embodiment of the first aspect of the present invention are provided compounds of Formula (I) according to the first embodiment of the first aspect wherein $R^1$ and $R^2$ are independently H or unsubstituted $C_{1-3}$alkyl or phenyl and $A^1$ and $A^2$ are independently $C_{1-4}$alkylene.

According to another embodiment of the first aspect of the present invention are provided compounds of Formula (I) according to the first embodiment of the first aspect wherein $-A^1-R^1$ and $-A^2-R^2$ together with the nitrogen to which they are attached form pyrrolyl, pyrrolinyl, pyrrolidinyl, piperidinyl, piperazinyl, morpholino, indolyl, isoindolyl, indolinyl, isoindolinyl, quinolinyl, dihydroquinolinyl, tetrahydroquinolinyl, isoquinolinyl, dihydroisoquinolinyl or tetrahydroisoquinolinyl and are optionally substituted with halo, $C_{1-4}$alkyl, $C_{1-4}$alkoxy, cyano or benzyl.

According to another embodiment of the first aspect of the present invention are provided compounds of Formula (I) according to the first embodiment of the first aspect wherein -$A^1$-$R^1$ and -$A^2$-$R^2$ together with the nitrogen to which they are attached form unsubstituted pyrrolyl, pyrrolinyl, pyrrolidinyl, piperidinyl, piperazinyl, morpholino, indolyl, isoindolyl, indolinyl, isoindolinyl, quinolinyl, dihydroquinolinyl, tetrahydroquinolinyl, isoquinolinyl, dihydroisoquinolinyl or tetrahydroisoquinolinyl.

According to another embodiment of the first aspect of the present invention are provided compounds of Formula (I) according to the first embodiment of the first aspect wherein -$A^1$-$R^1$ and -$A^2$-$R^2$ together with the nitrogen to which they are attached form unsubstituted pyrrolidinyl, piperidinyl, morpholino or isoindolinyl.

According to another embodiment of the first aspect of the present invention are provided compounds of Formula (I) according to the first embodiment of the first aspect wherein $R^3$ is H and m is 1.

According to another embodiment of the first aspect of the present invention are provided compounds of Formula (I) according to the first embodiment of the first aspect wherein n is 0.

According to another embodiment of the first aspect of the present invention are provided compounds of Formula (I) according to the first embodiment of the first aspect wherein $R^4$ and $R^5$ are halo.

According to another embodiment of the first aspect of the present invention are provided compounds of Formula (I) according to the first embodiment of the first aspect wherein $R^4$ is $C_{1-3}$alkyl and is attached to $G^1$.

According to another embodiment of the first aspect of the present invention are provided compounds of Formula (I) according to the first embodiment of the first aspect wherein $R^4$ is $C_{1-3}$perfluoroalkyl and is attached to $G^1$.

According to another embodiment of the first aspect of the present invention are provided compounds of Formula (I) according to the first embodiment of the first aspect wherein $R^4$ is hydrogen.

According to another embodiment of the first aspect of the present invention are provided compounds of Formula (I) according to the first embodiment of the first aspect wherein $R^4$ is fluoro.

According to another embodiment of the first aspect of the present invention are provided compounds of Formula (I) according to the first embodiment of the first aspect wherein $R^4$ is cyano.

According to another embodiment of the first aspect of the present invention are provided compounds of Formula (I) according to the first embodiment of the first aspect wherein $R^4$ is cyano or fluoro.

According to another embodiment of the first aspect of the present invention are provided compounds of Formula (I) according to the first embodiment of the first aspect wherein $R^4$ and $R^5$ are each fluoro.

According to another embodiment of the first aspect of the present invention are compounds of Formula (I) wherein the hydrogen atom attached to D is in the trans configuration to the hydrogen atom attached to E.

According to another embodiment of the first aspect of the present invention are compounds of Formula (I) wherein the hydrogen atom attached to D is in the cis configuration to the hydrogen atom attached to E.

According to another embodiment of the first aspect of the present invention are compounds of Formula (I) wherein D in relation to the four moieties to which it is attached has an absolute configuration of S; E in relation to the four moieties to which it is attached has an absolute configuration of S.

According to another embodiment of the first aspect of the present invention are compounds of Formula (I) wherein D in relation to the four moieties to which it is attached has an absolute configuration of S; E in relation to the four moieties to which it is attached has an absolute configuration of R.

According to another embodiment of the first aspect of the present invention are compounds of Formula (I) wherein D in relation to the four moieties to which it is attached has an absolute configuration of R; E in relation to the four moieties to which it is attached has an absolute configuration of S.

According to another embodiment of the first aspect of the present invention are compounds of Formula (I) wherein D in relation to the four moieties to which it is attached has an absolute configuration of R; E in relation to the four moieties to which it is attached has an absolute configuration of R.

According to another embodiment of the first aspect of the present invention are provided compounds of Formula (I) according to the first embodiment of the first aspect wherein $A^3$ is a bond.

According to another embodiment of the first aspect of the present invention are provided compounds of Formula (I) according to the first embodiment of the first aspect wherein $A^3$ is $C_{1-4}$alkylene.

According to another embodiment of the first aspect of the present invention are provided compounds of Formula (I) according to the first embodiment of the first aspect wherein $A^3$ is $C_{1-4}$alkylidene.

According to another embodiment of the first aspect of the present invention are provided compounds of Formula (I) according to the first embodiment of the first aspect wherein $A^3$ is methylene.

According to another embodiment of the first aspect of the present invention are provided compounds of Formula (I) according to the first embodiment of the first aspect wherein $A^4$ is a bond.

According to another embodiment of the first aspect of the present invention are provided compounds of Formula (I) according to the first embodiment of the first aspect wherein $A^4$ is methylene.

According to another embodiment of the first aspect of the present invention are provided compounds of Formula (I) according to the first embodiment of the first aspect wherein $A^4$ is attached $X^1$.

According to another embodiment of the first aspect of the present invention are provided compounds of Formula (I) according to the first embodiment of the first aspect wherein $A^4$ is attached X.

According to another embodiment of the first aspect of the present invention are provided compounds of Formula (I) according to the first embodiment of the first aspect wherein $R^4$ is attached X.

According to another embodiment of the first aspect of the present invention are provided compounds of Formula (I) according to the first embodiment of the first aspect wherein $A^1$ and $A^2$ are each independently $C_{1-4}$alkylene or a bond;
$A^3$ is a bond;
$A^4$ is a bond and is attached to $X^1$;
X and $X^1$ are each C;
$X^2$ and $X^3$ are each CH;
p is 0;
$R^1$ and $R^2$ are independently H, $C_{1-3}$alkyl, $C_{3-6}$cycloalkyl, phenyl, —O-phenyl, —N(H)C(O)O—$C_{1-4}$alkyl or $C_{1-4}$alkyl-N(H)C(O)O—;

said $C_{3-6}$cycloalkyl, phenyl or O-phenyl being independently and optionally substituted with $C_{1-4}$alkyl, $C_{1-3}$alkoxy or halo;

or are independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano;

or wherein -$A^1$-$R^1$ and -$A^2$-$R^2$ together with the nitrogen to which they are attached form pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, indolyl, isoindolyl, indolinyl, isoindolinyl, quinolinyl, dihydroquinolinyl, tetrahydroquinolinyl, isoquinolinyl, dihydroisoquinolinyl or tetrahydroisoquinolinyl and are optionally substituted with halo, $C_{1-4}$alkyl, $C_{1-4}$alkoxy, cyano or benzyl;

$R^3$ is H;

m is 1;

$R^4$ is hydrogen, cyano, halo, nitro, $C_{1-3}$alkyl or $C_{1-3}$perfluoroalkyl and is attached to X;

n is 0;

G is N;

$G^1$ is CH;

Y is (D)H wherein D is C; and

Z is (E)H wherein E is C;

provided that if $R^1$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^1$, then $A^1$ is $C_{2-4}$alkylene;

if $R^2$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^2$, then $A^2$ is $C_{2-4}$alkylene;

if $R^1$ is N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^2$ is H or $C_{1-3}$alkyl; and if $R^2$ is —N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^1$ is H or $C_{1-3}$alkyl.

According to various embodiments of a second aspect of the present invention are provided pharmaceutically acceptable formulations comprising compounds of Formula (I) as defined herein.

Disorders of particular interest include depression, attention deficit hyperactivity disorder, obsessive-compulsive disorder, post-traumatic stress disorder, substance abuse disorders and sexual dysfunction including (in particular) premature ejaculation. The compounds of the present invention may be administered alone or as part of a combination therapy.

Premature ejaculation may be defined as persistent or recurrent ejaculation before, upon or shortly after penile penetration of a sexual partner. It may also be defined as ejaculation occurring before the individual wishes [see *The Merck Manual*, 16$^{th}$ edition, p. 1576, published by Merck Research Laboratories, 1992].

Thus according to various embodiments of a third aspect of the present invention are provided methods of treating conditions selected from the group consisting of depression, attention deficit hyperactivity disorder, obsessive-compulsive disorder, post-traumatic stress disorder, substance abuse disorders and sexual dysfunction including and in particular premature ejaculation comprising the administration to a human in need thereof an effective amount of pharmaceutically acceptable formulations comprising compounds of the present invention as defined herein.

Other embodiments of the present invention may comprise suitable combinations of two or more of the embodiments and/or aspects disclosed herein.

Yet other embodiments and aspects of the invention will be apparent according to the description provided below.

DETAILED DESCRIPTION OF THE INVENTION

The description of the invention herein should be construed in congruity with the laws and principals of chemical bonding. For example, it may be necessary to remove a hydrogen atom in order accommodate a substitutent at any given location.

An embodiment or aspect which depends from another embodiment or aspect, will describe only the variables having values or provisos that differ from the embodiment or aspect from which it depends.

If a variable is quantified with a value of zero, then any bond attaching said variable should no longer be represented, e.g., if n in $(R^3)_n$ equals 0, then the bond attaching $R^3$ to G should no longer be represented.

As used herein, "halo" or "halogen" includes fluoro, chloro, bromo and iodo.

As used herein, "$C_{1-4}$alkylene" means a one to four carbon alkane having one hydrogen atom removed from two different carbon atoms in said alkane, e.g., —$CH_2CH_2CH_2$—.

As used herein, "$C_{1-4}$alkylidene" means a one to four carbon alkane having two hydrogen atoms removed from one carbon atom in said alkane, e.g.,

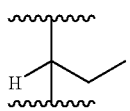

As used in the embodiments and claims herein the term "bond" is used as a means of eliminating an intervening variable to allow for a direct link between the remaining variables or atoms. For example, if where "$A^1$ and $A^2$ are each independently $C_{1-4}$alkylene or a bond" $A^1$ is a bond, then $R^1$ is attached to N via a single bond.

It should be understood that the alternating double bond designations in the six-membered ring of the 5,6-membered fused structure represented in Formula (I) are relative and represent the delocalized π orbital electrons of said ring.

It is to be understood that the present invention may include any and all possible stereoisomers, geometric isomers, diastereoisomers, enantiomers, anomers and optical isomers, unless a particular description specifies otherwise.

The compounds of this invention may exist in the form of pharmaceutically acceptable salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group may exist in the form of alkali metal salts such as, for example, a potassium salt and a sodium salt; alkaline earth metal salts such as, for example, a magnesium salt and a calcium salt; and salts with organic bases such as a trimethylammonium salt and an arginine salt. In the case of a sublingual formulation a saccharin salt or maleate salt may be of particular benefit. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

The dosage and dosage regimen and scheduling of a compounds of the present invention must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

Synthesis

Compounds of the present invention may be synthesized according to the general schema provided below. Variables provided in the schema below are defined in accordance with the description of compounds of the above Formulae unless otherwise specified.

A preferred method for the preparation of trans-cyclopentanes of Formula I is illustrated in Scheme 1. An appropriately substituted indole is condensed with a appropriately substituted unsaturated ketone in the presence of a catalyst such as ytterbium triflate hexahydrate to an indolyl ketone intermediate 1. Ketone 1 is then reductively condensed with an appropriately substituted amine in the presence of reagents such as sodium cyanoborohydride, sodium triacetoxyborohydride, or the like, to give a 3-indolyl cyclopentyl amine of Formula I.

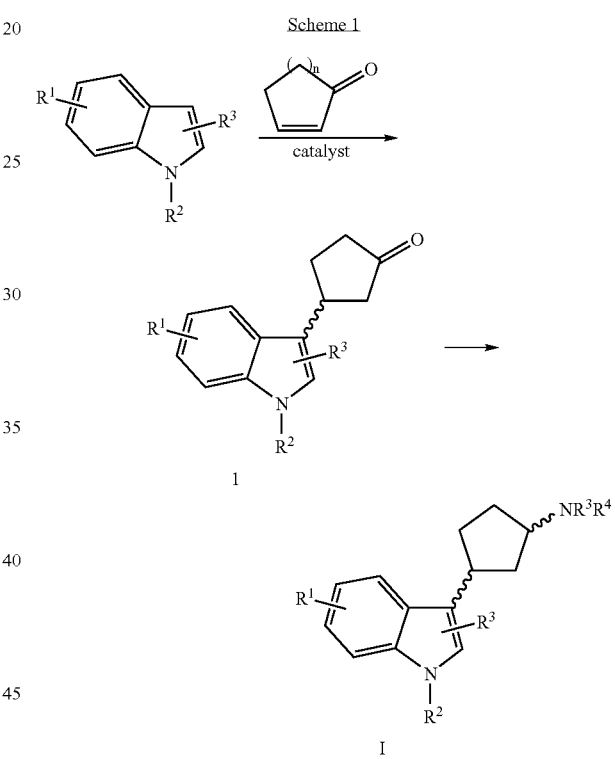

If desired, the intermediate Ketone 1 can be enzymatically resolved as described in Scheme 2. Racemic ketone 1 is incubated under appropriate conditions with an appropriate enzyme to selectively reduce the undesired ketone enantiomer to alcohol, 2. Alternatively, the desired ketone enantiomer can be selectively reduced to the alcohol 2. The resulting mixture can be separated by chromatography, recrystallization, or other methods know to those skilled in the art to give resolved ketone and resolved alcohol. The separated alcohol, 2, can be oxidized using reagents such as oxalyl chloride/DMSO, PCC, PDC, or the like, to give the opposite ketone enantiomer. Alternatively when the undesired ketone enantiomer is reduced to alcohol 2, the mixture can be reductively condensed with an appropriately substituted amine in the presence of reagents such as sodium cyanoborohydride, sodium triacetoxyborohydride, or the like, to give a 3-indolyl cyclopentyl amine of Formula I which is then separated from the undesired alcohol 2.

Scheme 2

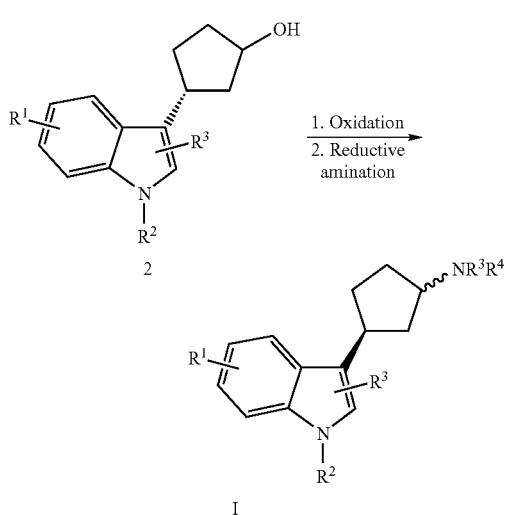

Scheme 3

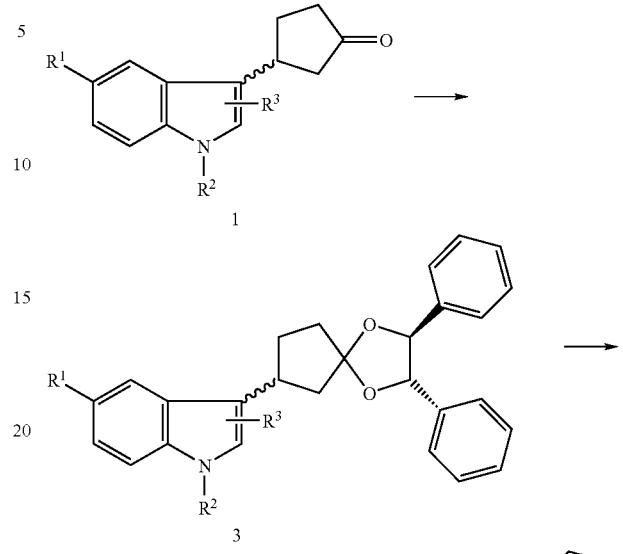

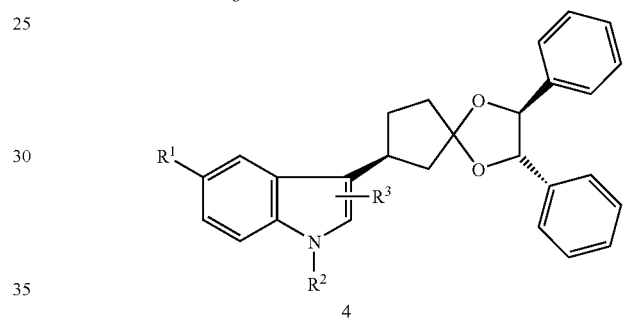

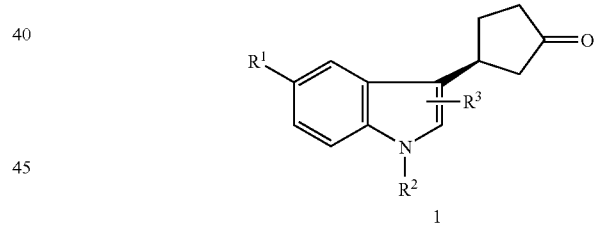

Another preferred method for the resolution of ketone intermediates 1 is illustrated in Scheme 3. Racemic ketone 1 is condensed with an optically active diol, such as (SS)-(−)-hydrobenzoin, to give a diastereomeric ketal intermediate 3. The single diastereomer of the ketal can be separated by methods known to those skilled in the art such as chromatography or recrystallization. Subsequent cleavage of the single diastereomer, 4, by hydrolysis, catalytic hydrogenation, or the like, provides resolved ketone intermediate 1.

INTERMEDIATES

Example 1

3-(3-oxocyclopentyl)-1H-indole-5-carbonitrile

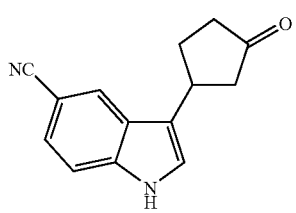

2-Cyclopenten-1-one (4.1 g, 4.2 mL, 50 mMol) was added to a stirred solution of 5-cyanoindole (1.42 g, 10 mMol) and ytterbium triflate hexahydrate (124 mg, 0.2 mMol) in acetonitrile (15 mL). After stirring at room temperature for 7d, the reaction was concentrated to an oil and diluted with ether. The red oily mixture was filtered through celite and the filtrate was concentrated in vacuo. The crude product was purified by flash chromatography on silica gel (35 g) using a gradient of 20–35% ethyl acetate in hexane. Pure product fractions were concentrated and dried under high vacuum to give 3-(3-oxocyclopentyl)-1H-indole-5-carbonitrile (1.55 g, 69%). $^1$H NMR (500 MHz, CDCl$_3$) δ 8.41 (1 H, bs), 7.99 (1 H, s), 7.45 (2 H, m), 7.12 (1 H, dd, J=2.44, 0.92 Hz), 3.72 (1 H, m), 2.77 (1 H, dd, J=7.63, 18.31 Hz), 2.56 (1 H, m), 2.40 (3 H, m), 2.10 (1 H, m). MS m/e 223.2 (M–H)$^+$. Anal. calcd. for C$_{14}$H$_{12}$N$_2$O: C, 74.98; H, 5.39; N, 12.49. Found: C, 74.75; H, 5.50; N, 12.23.

Example 2

3-(5-fluoro-1H-indol-3-yl)-cyclopentanone

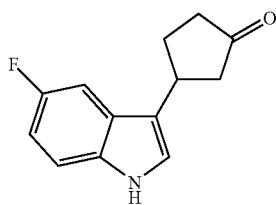

The method given in Example 1, using 5-fluoroindole (35.3 mMol), gave 3-(5-fluoro-1H-indol-3-yl)-cyclopentanone (1.29 g, 84%). $^1$H NMR (500 MHz, CDCl$_3$): δ 8.03 (1 H, bs), 7.30 (1 H, dd, J=8.85, 4.27), 7.26 (1 H, dd, J=9.46, 2.44), 7.04 (1 H, d, J=2.14), 6.97 (1 H, dt, J=8.85, 2.44), 3.66 (1 H, m), 2.75 (1 H, dd, J=7.32, 18.31 Hz), 2.53 (1 H, m), 2.42 (2 H, m), 2.34 (1 H, m), 2.11 (1 H, m). MS m/e 216.04 (M–H)$^+$. Anal. calcd. for C$_{13}$H$_{12}$NOF: C, 71.87; H, 5.56; N, 6.44. Found: C, 71.97; H, 5.69; N, 6.31.

Example 3

3-(4-Fluoro-1H-indol-3-yl)-cyclopentanone

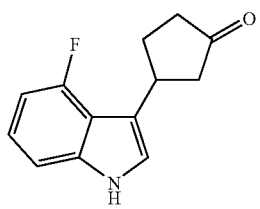

By the method of Example 1, using 4-fluoroindole (1.35 g, 10.0 mMol) as starting material, 3-(4-fluoro-1H-indol-3-yl)-cyclopentanone (700 mg, 32%) was obtained. $^1$H NMR (500 MHz, CDCl$_3$) δ ppm 2.09 (m, 1 H) 2.38 (m, 3 H) 2.51 (m, 1 H) 2.74 (dd, J=18.16, 7.78 Hz, 1 H) 3.81 (m, 1 H) 6.77 (dd, J=11.14, 7.78 Hz, 1 H) 6.94 (d, J=2.14 Hz, 1 H) 7.11 (m, 2 H) 8.13 (s, 1 H). MS m/e 216.2 (M–H)$^-$. Anal. calcd. for C$_{13}$H$_{12}$NOF: C, 71.87; H, 5.56; N, 6.44. Found: C, 71.90; H, 5.63; N, 6.29.

Example 4

3-(4-Bromo-1H-indol-3-yl)-cyclopentanone

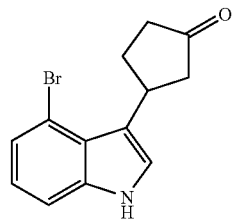

By the method of Example 1, using 4-bromoindole (1.96 g, 10.0 mMol) as starting material, 3-(4-bromo-1H-indol-3-yl)-cyclopentanone (405 mg, 15%) was obtained. $^1$H NMR (400 MHz, CDCl$_3$) δ ppm 2.09 (m, 1 H) 2.38 (m, 3 H) 2.56 (m, 1 H) 2.85 (dd, J=18.22, 7.46 Hz, 1 H) 4.32 (m, 1 H) 7.03 (m, 2 H) 7.30 (dd, J=7.46, 5.99 Hz, 2 H) 8.15 (s, 1 H). MS m/e 276.1 (M–H)$^-$. Anal. calcd. for C$_{13}$H$_{12}$NOBr: C, 56.13; H, 4.34; N, 5.03. Found: C, 56.23; H, 4.34; N, 5.14.

Example 5

3-(5-Chloro-1H-indol-3-yl)-cyclopentanone

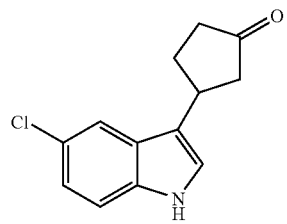

By the method of Example 1, using 5-chloroindole (1.52 g, 10.0 mMol) as starting material, 3-(5-chloro-1H-indol-3-yl)-cyclopentanone (1.09 g, 47%) was obtained. $^1$H NMR (400 MHz, CDCl3) δ ppm 2.09 (m, 1 H) 2.38 (m, 3 H) 2.52 (m, 1 H) 2.74 (dd, J=18.10, 7.58 Hz, 1 H) 3.66 (m, 1 H) 7.01 (d, J=1.71 Hz, 1 H) 7.16 (dd, J=8.80, 1.96 Hz, 1 H) 7.29 (d, J=9.29 Hz, 1 H) 7.58 (d, J=1.96 Hz, 1 H) 8.07 (s, 1 H). MS m/e 232.2 (M–H)$^-$. Anal. calcd. for C$_{13}$H$_{12}$NOCl: C, 66.81; H, 5.17; N, 5.99. Found: C, 67.10; H, 5.23; N, 5.75.

Example 6

3-(5-Bromo-1H-indol-3-yl)-cyclopentanone

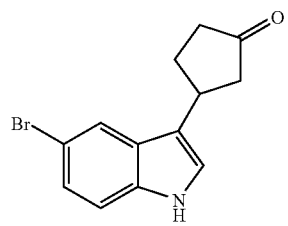

By the method of Example 1, using 5-bromoindole (1.96 g, 10.0 mMol) as starting material, 3-(5-bromo-1H-indol-3-yl)-cyclopentanone (1.30 g, 47%) was obtained. $^1$H NMR (500 MHz, CDCl3) δ ppm 2.08 (m, 1 H) 2.38 (m, 3 H) 2.52 (m, 1 H) 2.74 (dd, J=18.16, 7.48 Hz, 1 H) 3.65 (m, 1 H) 6.98 (d, J=2.14 Hz, 1 H) 7.24 (d, J=8.55 Hz, 1 H) 7.29 (dd, J=8.54, 1.84 Hz, 1 H) 7.74 (d, J=1.22 Hz, 1 H) 8.12 (s, 1 H).

MS m/e 276.2 (M–H)⁻. Anal. calcd. for C₁₃H₁₂NOCl: C, 56.13; H, 4.34; N, 5.03. Found: C, 56.18; H, 4.36; N, 4.97.

Example 7

3-(5-Iodo-1H-indol-3-yl)-cyclopentanone

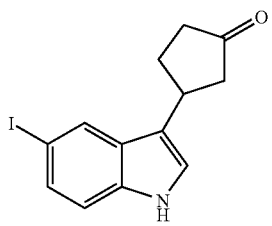

By the method of Example 1, using 5-iodoindole (2.43 g, 10.0 mMol) as starting material, 3-(5-iodo-1H-indol-3-yl)-cyclopentanone (1.34 g, 41%) was obtained. ¹H NMR (500 MHz, CDCl₃) δ ppm 2.08 (m, 1 H) 2.37 (m, 3 H) 2.52 (m, 1 H) 2.73 (dd, J=18.31, 7.32 Hz, 1 H) 3.64 (m, 1 H) 6.94 (d, J=2.14 Hz, 1 H) 7.15 (d, J=8.55 Hz, 1 H) 7.45 (dd, J=8.55, 1.53 Hz, 1 H) 7.95 (d, J=0.92 Hz, 1 H) 8.09 (s, 1 H). MS m/e 324.1 (M–H)⁻. Anal. calcd. for C₁₃H₁₂NOI: C, 48.02; H, 3.72; N, 4.30. Found: C, 48.01; H, 3.71; N, 4.25.

Example 8

3-(6-Fluoro-1H-indol-3-yl)-cyclopentanone

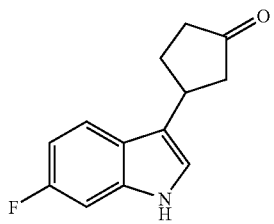

By the method of Example 1, using 6-fluoroindole (1.35 g, 10.0 mMol) as starting material, 3-(6-fluoro-1H-indol-3-yl)-cyclopentanone (1.6 g, 75%) was obtainee. ¹H NMR (500 MHz, CDCl3) δ ppm 2.10 (ddd, J=17.70, 12.51, 8.85 Hz, 1 H) 2.38 (m, 3 H) 2.52 (m, 1 H) 2.74 (dd, J=18.31, 7.32 Hz, 1 H) 3.68 (m, 1 H) 6.90 (td, J=9.16, 2.44 Hz, 1 H) 6.95 (d, J=1.53 Hz, 1 H) 7.05 (dd, J=9.61, 2.29 Hz, 1 H) 7.51 (dd, J=8.55, 5.19 Hz, 1 H) 8.05 (s, 1 H). MS m/e 216.2 (M–H)⁻. Anal. calcd. for C₁₃H₁₂NOF.0.35H₂O: C, 69.85; H, 5.73; N, 6.27. Found: C, 69.95; H, 5.73; N, 5.94.

Example 9

3-(6-Chloro-1H-indol-3-yl)-cyclopentanone

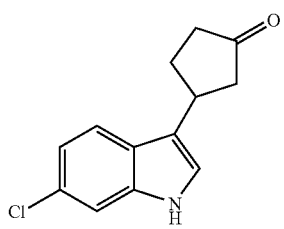

By the method of Example 1, using 6-chloroindole (1.52 g, 10.0 mMol) as starting material, 3-(6-chloro-1H-indol-3-yl)-cyclopentanone (1.01 g, 43%) was obtained. ¹H NMR (500 MHz, CDCl₃) δ ppm 2.09 (ddd, J=17.85, 12.51, 9.00 Hz, 1 H) 2.38 (m, 3 H) 2.52 (m, 1 H) 2.74 (dd, J=18.16, 7.48 Hz, 1 H) 3.68 (ddd, J=16.25, 8.93, 6.87 Hz, 1 H) 6.97 (dd, J=2.29, 0.76 Hz, 1 H) 7.10 (dd, J=8.55, 1.83 Hz, 1 H) 7.36 (d, J=1.53 Hz, 1 H) 7.51 (d, J=8.55 Hz, 1 H) 8.06 (s, 1 H). MS m/e 232.2 (M–H)⁻. Anal. calcd. for C₁₃H₁₂NOCl: C, 66.81; H, 5.17; N, 5.99. Found: C, 66.74; H, 5.06; N, 5.87.

Example 10

3-(6-Bromo-1H-indol-3-yl)-cyclopentanone

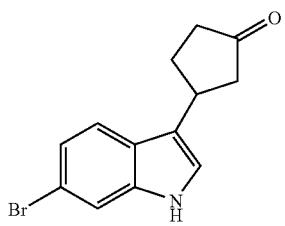

By the method of Example 1, using 6-bromoindole (1.96 g, 10.0 mMol) as starting material, 3-(6-bromo-1H-indol-3-yl)-cyclopentanone (0.95 g, 34%) was obtained. ¹H NMR (500 MHz, CDCl₃) δ ppm 2.09 (ddd, J=17.78, 12.44, 9.16 Hz, 1 H) 2.38 (m, 3 H) 2.52 (m, 1 H) 2.74 (dd, J=18.31, 7.63 Hz, 1 H) 3.68 (m, 1 H) 6.96 (d, J=1.83 Hz, 1 H) 7.23 (dd, J=8.39, 1.68 Hz, 1 H) 7.47 (d, J=8.54 Hz, 1 H) 7.53 (d, J=1.83 Hz, 1 H) 8.01 (br s, 1 H). MS m/e 276.1 (M–H)⁻. Anal. calcd. for C₁₃H₁₂NOBr: C, 56.13; H, 4.34; N, 5.03. Found: C, 56.26; H, 4.35; N, 4.88.

Example 11

3-(7-Fluoro-1H-indol-3-yl)-cyclopentanone

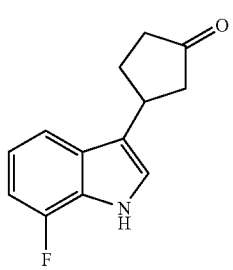

By the method of Example 1, using 7-fluoroindole (405 mg, 3.0 mMol) as starting material, 3-(7-fluoro-1H-indol-3-yl)-cyclopentanone (526 mg, 81%) was obtained. ¹H NMR (500 MHz, CDCl₃) δ ppm 2.13 (ddd, J=17.85, 12.36, 9.16 Hz, 1 H) 2.40 (m, 3 H) 2.54 (m, 1 H) 2.77 (dd, J=18.16, 7.48 Hz, 1 H) 3.70 (m, 1 H) 6.94 (dd, J=11.29, 7.63 Hz, 1 H) 7.05 (m, 2 H) 7.39 (d, J=7.63 Hz, 1 H) 8.18 (br s, 1 H). MS m/e 216.1 (M–H)⁻.

Example 12

3-(7-Chloro-1H-indol-3-yl)-cyclopentanone

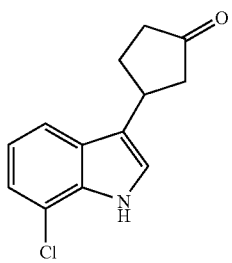

By the method of Example 1, using 7-chloroindole (1.0 g, 6.6 mMol) as starting material, 3-(7-chloro-1H-indol-3-yl)-cyclopentanone (479 mg, 31%) was obtained. $^1$H NMR (400 MHz, CDCl$_3$) δ ppm 2.11 (ddd, J=17.85, 12.35, 9.17 Hz, 1 H) 2.39 (m, 3 H) 2.53 (m, 1 H) 2.76 (dd, J=17.97, 7.46 Hz, 1 H) 3.69 (ddd, J=16.38, 9.05, 6.85 Hz, 1 H) 7.04 (dd, J=2.69, 1.22 Hz, 1 H) 7.08 (2s, 1 H) 7.22 (dd, J=7.70, 0.86 Hz, 1 H) 7.52 (d, J=8.07 Hz, 1 H) 8.26 (s, 1 H). MS m/e 232.1 (M–H)$^-$. Anal. calcd. for C$_{13}$H$_{12}$NOCl: C, 66.81; H, 5.17; N, 5.99. Found: C, 66.78; H, 5.19; N, 6.03.

Example 13

3-(7-Bromo-1H-indol-3-yl)-cyclopentanone

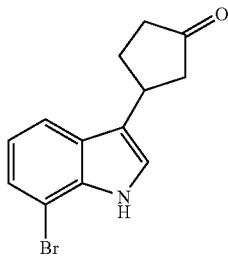

By the method of Example 1, using 7-bromoindole (1.09 g, 5.56 mMol) as starting material, 3-(7-bromo-1H-indol-3-yl)-cyclopentanone (527 mg, 34%) was obtained. $^1$H NMR (500 MHz, CDCl$_3$) δ ppm 2.11 (ddd, J=18.08, 12.44, 9.16 Hz, 1 H) 2.39 (m, 3 H) 2.53 (m, 1 H) 2.76 (dd, J=18.16, 7.48 Hz, 1 H) 3.69 (m, 1 H) 7.02 (t, J=7.78 Hz, 1 H) 7.05 (d, J=2.44 Hz, 1 H) 7.37 (d, J=7.63 Hz, 1 H) 7.56 (d, J=7.93 Hz, 1 H) 8.18 (br s, 1 H). MS m/e 276.1 (M–H)$^-$. Anal. calcd. for C$_{13}$H$_{12}$NOBr: C, 56.13; H, 4.13; N, 5.03. Found: C, 56.02; H, 4.14; N, 4.83.

Example 14

Chiral HPLC Resolution of 3-(3-Oxocyclopentyl)-1H-indole-5-carbonitrile

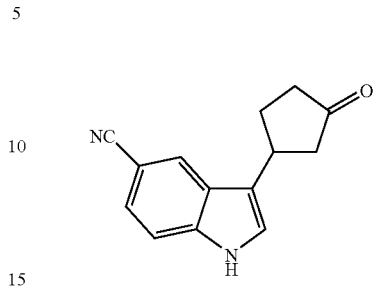

The (1S)- and (1R)-enantiomers of 3-(3-oxocyclopentyl)-1H-indole-5-carbonitrile were resolved by chiral HPLC on a Chiral Technologies Chiralcel OD column (20μ, 50×500 mm) using a mobile phase gradient of ethanol/hexane (10–100% containing 0.01% diethylamine). Flow rate was varied over the gradient from 60–50 mL/min. The first isomer to elute was (1S)-3-(3-oxocyclopentyl)-1H-indole-5-carbonitrile ([α]$^{25}$ −24.4 (589 nm, c 2.62 mg/mL, MeOH); t$_R$ 10.8 min*). The second isomer to elute was (1R)-3-(3-oxocyclopentyl)-1H-indole-5-carbonitrile ([α]$^{25}$ +10.5 (589 nm, c 2.64 mg/mL, EtOH); t$_R$ 12.5 min*).

*Chiral Technologies Chiralcel OD analytical column (4.6×25 mm), 15% ethanol in hexane containing 0.1% diethylamine, flow rate 1.0 mL/min.

Example 15

Enzymatic resolution of 3-(3-Oxocyclopentyl)-1H-indole-5-carbonitrile

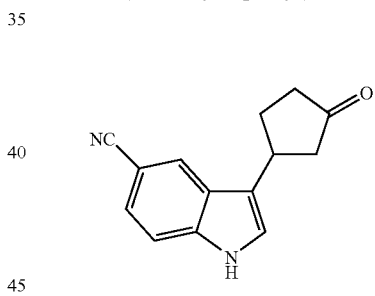

Alternatively, (1S)-3-(3-oxocyclopentyl)-1H-indole-5-carbonitrile was obtained by enzymatic resolution of racemic 3-(3-oxocyclopentyl)-1H-indole-5-carbonitrile utilizing ketoreductase KRED-1004 (Biocatalytics, Inc., Pasadena, Calif.) in the presence of isopropanol as co-substrate and NADPH as cofactor. The 1 L reaction mixture consisted of 10 mM potassium phosphate buffer (pH 6.0), 15% methanol, 2% isopropanol, 50 mg NADPH, 50 mg KRED-1004 and 500 mg 3-(3-oxocyclopentyl)-1H-indole-5-carbonitrile in water. After incubating at 30° C., 75 rpm for 3 d, the reaction reached completion by RP-HPLC analysis. The reaction mixture was then extracted with 1 L of ethyl acetate to afford 516 mg mixture of (1S)-3-(3-oxocyclopentyl)-1H-indole-5-carbonitrile and (1R,3S)-3-(3-hydroxy-cyclopentyl)-1H-indole-5-carbonitrile. The enantio excess (ee) of (1S)-3-(3-oxocyclopentyl)-1H-indole-5-carbonitrile was determined to be greater than 95% by chiral HPLC.

The ketone/alcohol mixture (2.4 g) was purified by flash chromatography on 110 g silica gel with a step gradient of 0, 1, and 2% methanol in methylene chloride. The two components were concentrated and dried under high vacuum to yield (1S)-3-(3-oxocyclopentyl)-1H-indole-5-carbonitrile (1.1 g, 46%) and (1R,3S)-3-(3-hydroxycyclopentyl)-1H-indole-5-carbonitrile (0.94 g, 39%). (The configuration of the alcohol was determined to be cis by a NOE method.)

Analytical data for (1S)-3-(3-oxocyclopentyl)-1H-indole-5-carbonitrile: $^1$H NMR (500 MHz, CDCl$_3$) δ 8.38 (1 H, bs), 7.98 (1 H, s), 7.45 (2 H, m), 7.11 (1 H, dd, J=2.44, 0.91 Hz), 3.71 (1 H, m), 2.77 (1 H, dd, J=7.63, 18.31 Hz), 2.56 (1 H, m), 2.40 (3 H, m), 2.10 (1 H, m). MS m/e 223.2 (M–H)$^+$. $[α]^{25}$ –22.3 (589 nm, c 1.54 mg/mL, MeOH).

Analytical data for (1R,3S)-3-(3-hydroxycyclopentyl)-1H-indole-5-carbonitrile: $^1$H NMR (500 MHz, CDCl$_3$) δ 8.26 (1 H, bs), 8.04 (1 H, s), 7.40 (2 H, m), 7.15 (1 H, dd, J=2.44, 0.91 Hz), 4.52 (1 H, m), 3.31 (1 H, p, J=8.24), 2.55 (1 H, m), 2.15 (1 H, m), 1.98 (2 H, m), 1.83 (1 H, m), 1.76 (1 H, m). MS m/e 225.2 (M–H)$^+$. Anal. calcd. for C$_{14}$H$_{14}$N$_2$O.0.65 H$_2$O: C, 70.66; H, 6.48; N, 11.77. Found: C, 70.87; H, 6.80; N, 11.44. $[α]^{25}$ –13.8 (589 nm, c 1.54 mg/mL, MeOH).

Example 16

Separation of (3S)-3-(5-fluoro-1H-indol-3-yl)-cyclopentanone from its racemic mixture

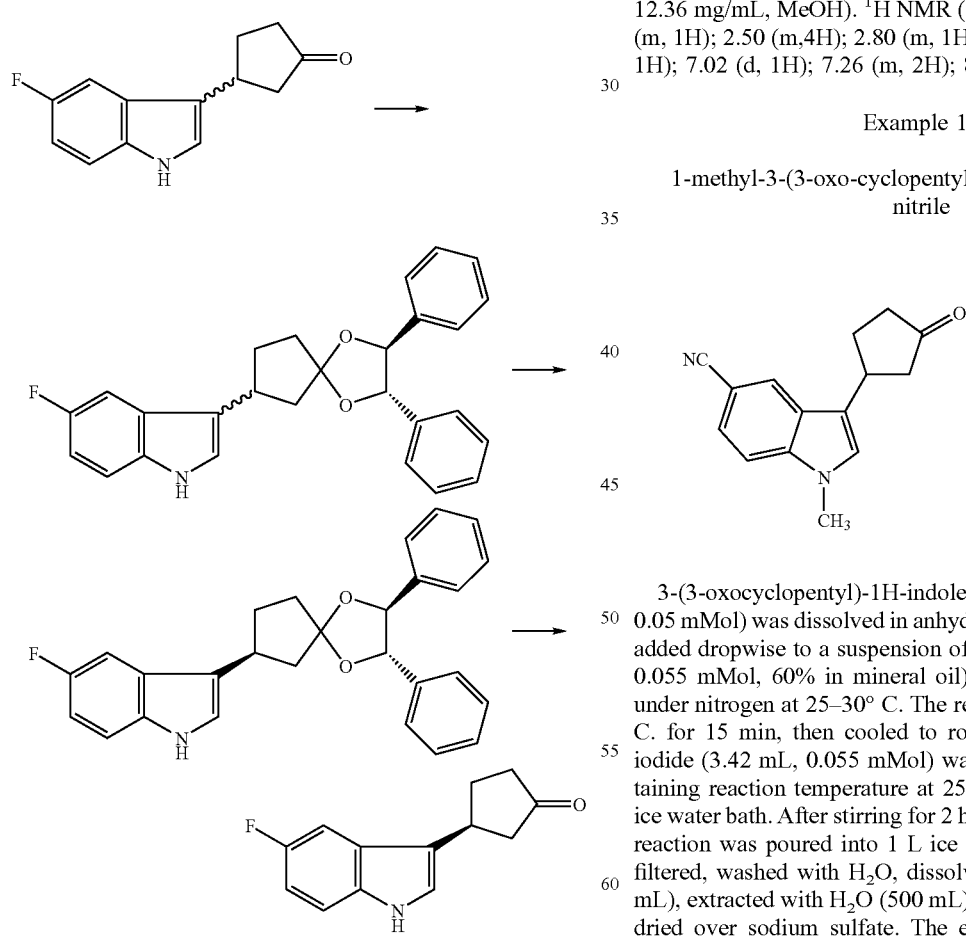

A solution of racemic 3-(5-fluoro-1H-indol-3-yl)-cyclopentanone (5 g, 23 mMol), (S,S)-(−) hydrobenzoin (5 g, 23 mMol) and p-toluenesulfonic acid monohydrate (0.44 g, 2.3 mMol) in of benzene (150 mL) was heated to reflux under a Dean-Stark trap for 40 min. The reaction mixture was concentrated and the residue was purified by chromatography on silica gel using ethyl acetate/hexane (0%–20%) as the eluent. The pure fractions were concentrated to give a mixture of two diastereomers (5 g, 53%). The mixture was dissolved in ethyl acetate (5 mL) and diluted with hexane (30 mL). The resulting solution was cooled in a refrigerator for 2 d to give the crystalline single diastereomer, (3S)-3-(5-fluoro-1H-indol-3-yl)-cyclopentanone (S,S)-hydrobenzoin ketal (1.6 g, 86.8% de by chiral HPLC). $[α]^{25}$ –7.35 (589 nm, c 6.04 mg/mL, MeOH). $^1$HNMR (500 MHz, CDCl$_3$) δ 1.98 (m, 1H); 2.36 (m,4H); 2.67 (m,1H); 3.50 (m, 1H); 4.75 (s, 2H); 6.94 (t, 1H); 7.09 (s, 1H); 7.30 (m, 11H); 7.93 (s, 1H). M−1=412.

A solution of the above ketal (207 mg, 0.5 mMol) in methanol (35 mL) and 3N HCl (1 mL) was stirred for 18 hr. The solution was concentrated and the residue was dissolved in ethyl acetate. The solution was washed with aqueous sodium bicarbonate, washed with brine, and dried over magnesium sulfate. The solution was concentrated to give the crude product which was purified by chromatography on silica gel using ethyl acetate/hexane (0–50%) as the eluent to give (3S)-3-(5-fluoro-1H-indol-3-yl)-cyclopentanone (68 mg, 63%, 81% ee by chiral HPLC. $[α]^{25}$ –10.67 (589 nm, c 12.36 mg/mL, MeOH). $^1$H NMR (500 MHz, CDCl$_3$) δ 2.09 (m, 1H); 2.50 (m,4H); 2.80 (m, 1H); 3.64 (m, 1H); 6.96 (m, 1H); 7.02 (d, 1H); 7.26 (m, 2H); 8.20 (s,1H). M+1=218.

Example 17

1-methyl-3-(3-oxo-cyclopentyl)-1H-indole-5-carbonitrile

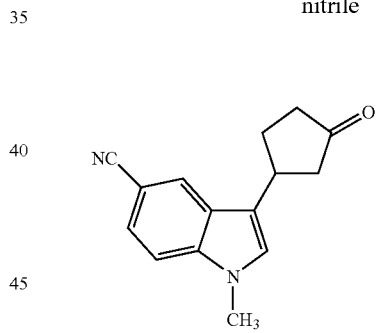

3-(3-oxocyclopentyl)-1H-indole-5-carbonitrile (11.21 g, 0.05 mMol) was dissolved in anhydrous DMSO (30 mL) and added dropwise to a suspension of sodium hydride (2.25 g, 0.055 mMol, 60% in mineral oil) in dry DMSO (50 mL) under nitrogen at 25–30° C. The reaction was heated to 40° C. for 15 min, then cooled to room temperature. Methyl iodide (3.42 mL, 0.055 mMol) was added dropwise, maintaining reaction temperature at 25–30° C. with an external ice water bath. After stirring for 2 h at room temperature, the reaction was poured into 1 L ice water. The tan solid was filtered, washed with H$_2$O, dissolved in ethyl acetate (750 mL), extracted with H$_2$O (500 mL) and brine (500 mL), and dried over sodium sulfate. The ethyl acetate extract was concentrated in vacuo and the product was purified by chromatography on silica gel with a 10% step gradient of 25–45% ethyl acetate in hexane. Pure product fractions were concentrated in vacuo and dried under high vacuum to give 1-methyl-3-(3-oxo-cyclopentyl)-1H-indole-5-carbonitrile (8.52 g, 72%). $^1$H NMR (500 MHz, CDCl$_3$) δ 7.95 (1 H, s), 7.46 (1 H, dd, J=8.54, 1.22), 7.34 (1 H, d, J=8.54), 6.94 (1 H, s), 3.78 (3 H, s), 3.69 (1 H, m), 2.74 (1 H, dd, J=7.63, 18.01 Hz), 2.53 (1 H, m), 2.38 (3 H, m), 2.06 (1 H, m). MS m/e 239.3 (M+H)$^+$. Anal. calcd. for C$_{15}$H$_{14}$N$_2$O: C, 75.60; H, 5.92; N, 11.75. Found: C, 75.31; H, 5.86; N, 11.55. IR (KBr) 2219, 1728 cm$^{-1}$.

Example 18

1-Ethyl-3-(3-oxo-cyclopentyl)-1H-indole-5-carbonitrile

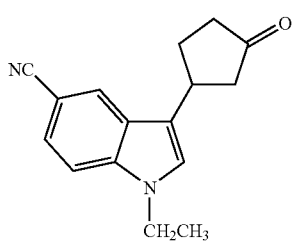

1-Ethyl-3-(3-oxo-cyclopentyl)-1H-indole-5-carbonitrile (1.96 g, 70%) was prepared by the previous example on a 10 mMol scale using iodoethane. $^1$H NMR (500 MHz, CDCl$_3$) δ 7.94 (1 H, s), 7.43 (1 H, dd, J=8.55, 1.53), 7.35 (1 H, d, J=8.55), 7.01 (1 H, s), 4.15 (2 H, q, J=7.32), 3.68 (1 H, m), 2.73 (1 H, dd, J=7.63, 18.00 Hz), 2.52 (1 H, m), 2.36 (3 H, m), 2.07 (1 H, m), 1.45 (3 H, t, J=7.32). MS m/e 253.4 (M+H)$^+$. Anal. calcd. for C$_{16}$H$_{16}$N$_2$O.0.14 EtOAc: C, 75.16; H, 6.52; N, 10.59. Found: C, 74.90; H, 6.15; N, 10.68. IR (KBr) 2218, 1739, 2974 cm$^{-1}$.

Synthesis of Compounds of Formula (I)

Example 19

General Example for the synthesis of 3-(3-alkylaminocyclopentyl)-1H-indole-5-carbonitriles and 3-(3-dialkylaminocyclopentyl)-1H-indole-5-carbonitriles

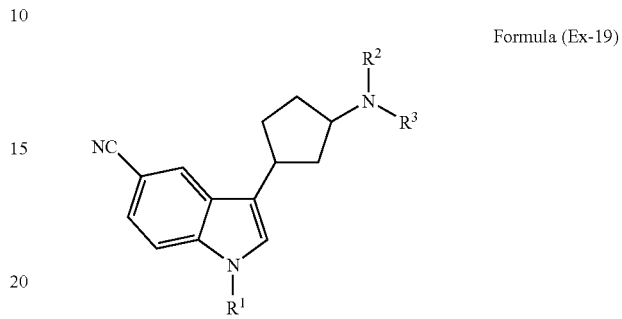

Formula (Ex-19)

3-(3-oxocyclopentyl)-1H-indole-5-carbonitrile, 1-methyl-3-(3-oxo-cyclopentyl)-1H-indole-5-carbonitrile, or 1-ethyl-3-(3-oxo-cyclopentyl)-1H-indole-5-carbonitrile (0.5 mMol) and the amine (R$^2$R$^3$NH, 5.0 mMol) were dissolved in ethanol to a final volume of 5 mL. After stirring for 15 min, sodium triacetoxyborohydride (430 mg, 2.0 mMol) was added and the reaction stirred for 3 h. (In the case of primary amines (R$^2$NH$_2$), the reactions were catalyzed by the addition of 3 drops glacial HOAc. In some cases, additional reaction time was necessary for completion.) The reaction was then diluted with water (10 mL) and extracted three times with ethyl acetate (10 mL). The organic extracts were dried over sodium sulfate and concentrated in vacuo. The residue was purified by preparative reverse phase HPLC to give the product as an oily trifluoroacetic acid salt of cis/trans diastereomers. Where indicated, the free base was isolated by extraction of the TFA salt from saturated sodium carbonate solution with ethyl acetate.

The following compounds of Formula (Ex-19) were prepared by the above method:

| Cmpd. | R$^1$ | R$^2$ | R$^3$ | Form | Yield (%) | MH$^+$ | LCMS t$_R$, min. | HPLC method* |
|---|---|---|---|---|---|---|---|---|
| 1 | H | H | Me | TFA | 50 | 240.12 | 0.870 | A |
| 2 | H | H | Et | TFA | 63 | 254.11 | 0.903 | A |
| 3 | H | Me | Me | TFA | 95 | 254.12 | 0.867 | A |
| 4 | H | Me | Et | TFA | 36 | 268.13 | 0.903 | A |
| 5 | H | Et | Et | TFA | 35 | 282.15 | 0.980 | A |
| 6 | H | —(CH$_2$)$_4$— | | TFA | 42 | 280.13 | 0.953 | A |
| 7 | H | (benzyl-fused ring) | | Base | 43 | 328.24 | 1.220 | B |
| 8 | H | (benzyl-fused ring) | | Base | 44 | 342.20 | 1.293 | B |
| 9 | H | H | —(CH$_2$)$_2$Ph | Base | 50 | 330 | 1.673 | C |
| 10 | H | Me | —(CH$_2$)$_2$Ph | Base | 54 | 344 | 1.643 | C |
| 11 | H | —(CH$_2$)$_2$—O—(CH$_2$)$_2$— | | Base | 27 | 296 | 1.093 | C |

-continued

| Cmpd. | R¹ | R² | R³ | Form | Yield (%) | MH⁺ | LCMS $t_R$, min. | HPLC method* |
|---|---|---|---|---|---|---|---|---|
| 12 | H | Me | —CH₂Ph | Base | 80 | 330 | 2.097 | C |
| 13 | H | H | —CH₂Ph | Base | 43 | 316 | 1.590 | C |
| 14 | H |  | —(CH₂)₅— | Base | 79 | 294 | 1.840 | C |
| 15 | H | n-Pr | n-Pr | Base | 29 | 310 | 2.007 | C |
| 16 | H | H | n-Pr | Base | 40 | 268 | 1.887 | C |
| 17 | Me | H | Me | Base | 36 | 254.24 | 1.163 | B |
| 18 | Me | H | Et | Base | 48 | 268.26 | 1.203 | B |
| 19 | Me | H | —CH₂Ph | Base | 47 | 330.24 | 1.400 | B |
| 20 | Me | H | —(CH₂)₂Ph | Base | 41 | 344.26 | 1.473 | B |
| 21 | Me | Me | Me | Base | 67 | 268.26 | 1.150 | B |
| 22 | Me | Me | Et | Base | 69 | 282.22 | 1.163 | B |
| 23 | Me | Et | Et | Base | 29 | 296.31 | 1.220 | B |
| 24 | Me |  | —(CH₂)₄— | Base | 76 | 294.24 | 1.187 | B |
| 25 | Me |  | —(CH₂)₅— | Base | 80 | 308.22 | 1.203 | B |
| 26 | Me |  | —(CH₂)₂—O—(CH₂)₂— | Base | 60 | 310.20 | 1.143 | B |
| 27 | Me | Me | —CH₂Ph | Base | 76 | 344.20 | 1.357 | B |
| 28 | Me | Me | —(CH₂)₂Ph | Base | 70 | 358.30 | 1.477 | B |
| 29 | Me | H | n-Pr | Base | 10 | 282.29 | 1.300 | B |
| 30 | Me | n-Pr | n-Pr | Base | 58 | 324.30 | 1.340 | B |
| 31 | Et | Me | Bn | Base | 30 | 358 | 1.743 | C |
| 32 | Et | Me | Me | Base | 27 | 282 | 1.460 | C |

*HPLC Methods:
A. Gradient conditions for YMC ODS-A C18 S7 3.0 × 50 mm:
Solvent A 10% MeOH-90% H2O-0.1% TFA
Solvent B 90% MeOH-10% H2O-0.1% TFA
0–100% B, 2 m gradient time, 1 m hold at 100% B.
Flow rate 5 mL/min.
B. Gradient conditions for XTERRA C18 S5 4.6 × 50 mm:
Solvent A 10% MeOH-90% H2O-0.1% TFA
Solvent B 90% MeOH-10% H2O-0.1 TFA
0–100% B, 2 m gradient time, 1 m hold at 100% B.
Flow rate 5 mL/min.
C. Gradient conditions for XTERRA S7 3.0 × 50 mm:
Solvent A 10% MeOH-90% H2O-0.1% TFA
Solvent B 90% MeOH-10% H2O-0.1% TFA
0–100% B, 3 min. gradient time, 1 mim hold at 100% B.
Flow rate 4 mL/min.

Example 20

General Example for synthesis of 3-(5-Fluoro-1H-indol-3-yl)-cyclopentyl-dialkylamines

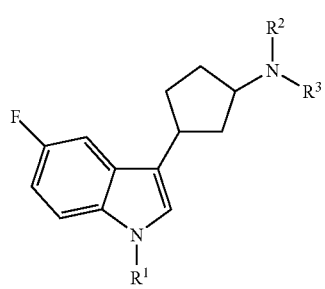

Formula (Ex-20)

3-(5-fluoro-1H-indol-3-yl)-cyclopentanone (0.5 mMol) and amine (R²R³NH, 5.0 mMol) were dissolved in EtOH to a final volume of 5 mL. After stirring for 15 min., sodium triacetoxyborohydride (430 mg, 2.0 mMol) was added and the reaction continued for 2–3 d. In some cases, additional reaction time was necessary for completion.) The reaction was then diluted with 10 mL water and extracted three times with 10 mL EtOAc. The organic layers were pooled, dried over Na₂SO₄, and concentrated under vacuum. Purification by preparative reverse phase HPLC gave the product as an oily trifluoroacetic acid salt.

The above procedure was followed for each of the following compounds of Formula (Ex-20):

| Cmpd. | R¹ | R² | R³ | Form | Yield (%) | MH⁺ | LCMS $t_R$, min.* |
|---|---|---|---|---|---|---|---|
| 33 | H | Me | Me | TFA | 71 | 247.2 | 0.943 |
| 34 | H | Et | Me | TFA | 72 | 261.2 | 0.990 |
| 35 | H | Et | Et | TFA | 63 | 275.2 | 1.013 |
| 36 | H | —(CH₂)₄— |  | TFA | 53 | 273.2 | 0.993 |

*HPLC Method:
YMC ODS-A C18 57 3.0 × 50 mm column;
Solvent A 10% MeOH-90% H2O-0.1% TFA
Solvent B 90% MeOH-10% H2O-0.1% TFA
0–100% B, 2 m gradient time, 1 m hold at 100% B.
Flow rate 5 mL/min.

Example 21

Specific procedure for the synthesis of 3-(3-Dimethylaminocyclopentyl)-1H-indole-5-carbonitrile

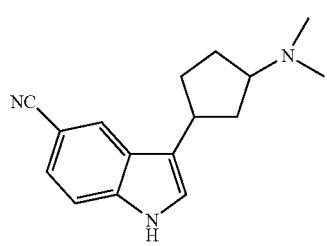

Compound 3

3-(3-oxocyclopentyl)-1H-indole-5-carbonitrile (2.24 g, 10 mMol) and dimethylamine (2.0 M solution in THF, 50 mL, 100 mMol) were dissolved in EtOH (150 mL). After stirring for 15 min, sodium triacetoxyborohydride (8.50 g, 40 mMol) was added and the reaction stirred for 4 h. The reaction was then diluted with water (100 mL) and made acidic (pH 3) with HCl (6 M). The reaction was then adjusted to pH 10 with sodium carbonate. It was extracted three times with ethyl acetate (100 mL) and the organic extracts were dried over sodium sulfate, concentrated in vacuo, and dried under high vacuum to give 3-(3-dimethylaminocyclopentyl)-1H-indole-5-carbonitrile (Compound 3, 2.5 g, 100%) as mixture of cis/trans diastereomers. $^1$H NMR (500 MHz, d4-MeOH) δ 8.02 (0.7 H s), 7.99 (0.3 H, s), 7.46 (0.4 H, s), 7.44 (0.6 H, s), 7.35 (1 H, dd, J=8.55 1.53), 7.24 (0.7 H, s), 7.21 (0.3 H, s), 3.49 (0.4 H, m), 3.37 (0.6 H, m), 2.92 (0.3 H, m), 2.83 (0.7 H, m), 2.41 (0.7 H, m), 2.36 (6 H, s), 2.22 (1.3 H, m), 2.07 (1 H, m), 1.80 (2 H, m), 1.67 (1 H, m). MS m/e 254.2 (M+H)$^+$, 252.2 (M−H)$^+$. LCMS (YMC ODS-A C18 S7 3.0×50 mm) $t_R$, 0.857 min., MH$^+$ 254.19.

Example 22

3-(4-Fluoro-1H-indol-3-yl)-cyclopentyl-dimethylamine

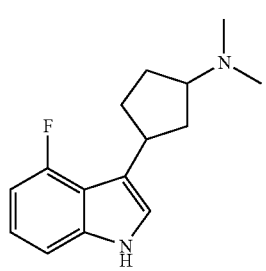

Compound 37

By the method of Example 21, using 3-(4-fluoro-1H-indol-3-yl)-cyclopentanone (217 mg, 1.0 mMol) as starting material, 3-(4-fluoro-1H-indol-3-yl)-cyclopentyl-dimethylamine (77 mg, 31%) was obtained. $^1$H NMR (400 MHz, d$^4$MeOH) δ ppm 1.90 (m, 4 H) 2.23 (m, 3 H) 2.54 (m, 1 H) 2.81 (m, 6 H) 3.57 (m, 2 H) 6.63 (m, 1 H) 7.07 (m, 3 H). LCMS (XTERRA C18 S5 4.6×50 mm) $t_R$, 1.153 min., MH$^+$ 247.28.

Example 23

3-(4-Bromo-1H-indol-3-yl)-cyclopentyl-dimethylamine

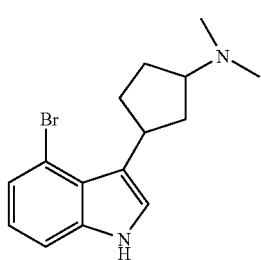

Compound 38

By the method of Example 21, using 3-(4-bromo-1H-indol-3-yl)-cyclopentanone (278 mg, 1.0 mMol) as starting material, 3-(4-bromo-1H-indol-3-yl)-cyclopentyl-dimethylamine (131 mg, 43%) was obtained. $^1$H NMR (500 MHz, d$^4$MeOH) δ ppm 1.93 (m, 2 H) 2.27 (m, 3 H) 2.67 (m, 1 H) 2.87 (d, J=3.66 Hz, 6 H) 3.70 (m, 1 H) 4.06 (m, 1 H) 6.95 (t, J=7.93 Hz, 1 H) 7.17 (m, 1 H) 7.32 (m, 2 H). LCMS (XTERRA C18 S5 4.6×50 mm) $t_R$, 1.373 min., MH$^+$ 307.19, 309.19.

Example 24

3-(5-Chloro-1H-indol-3-yl)-cyclopentyl-dimethylamine

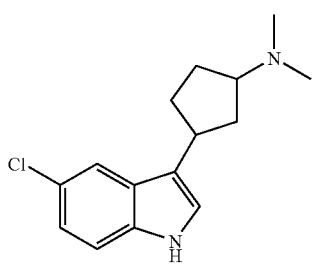

Compound 39

By the method of Example 21, using 3-(5-chloro-1H-indol-3-yl)-cyclopentanone (234 mg, 1.0 mMol) as starting material, 3-(5-chloro-1H-indol-3-yl)-cyclopentyl-dimethylamine (83 mg, 32%) was obtained. $^1$H NMR (400 MHz, d4MeOH) δ ppm 1.85 (m, 2 H) 2.28 (m, 3 H) 2.60 (m, 1 H) 2.84 (s, 6 H) 3.60 (m, 2 H) 7.03 and 7.05 (2d, J=1.96 Hz, 1 H) 7.12 and 7.15 (2s, 1 H) 7.27 and 7.29 (2s, 1 H) 7.52 and 7.54 (2d, J=1.83 Hz, 1 H). LCMS (XTERRA C18 S5 4.6×50 mm) $t_R$, 1.260 min., MH$^+$ 263.24.

Example 25

3-(5-Bromo-1H-indol-3-yl)-cyclopentyl-dimethylamine

Compound 40

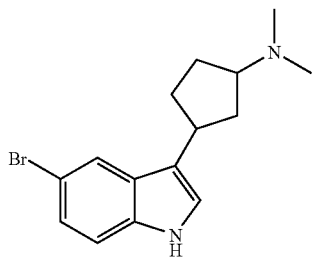

By the method of Example 21, using 3-(5-bromo-1H-indol-3-yl)-cyclopentanone (278 mg, 1.0 mMol) as starting material, 3-(5-bromo-1H-indol-3-yl)-cyclopentyl-dimethylamine (248 mg, 81%) was obtained. $^1$H NMR (400 MHz, d4-MeOH) δ ppm 1.74 (m, 3 H) 2.11 (m, 3 H) 2.39 (s, 6 H) 2.93 (m, 1 H) 3.32 (m, 1 H) 7.06 (2s, 1 H) 7.13 (2t, J=1.71 Hz, 1 H) 7.22 (2s, 1 H) 7.66 (2d, J=1.47 Hz, 1 H). LCMS (XTERRA C18 S5 4.6×50 mm) $t_R$, 1.307 min., MH$^+$ 307.21.

Example 26

3-(5-Iodo-1H-indol-3-yl)-cyclopentyl-dimethylamine

Compound 41

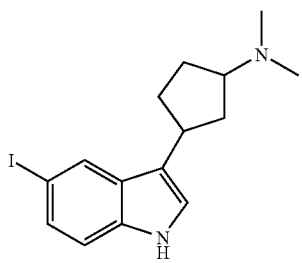

By the method of Example 21, using 3-(5-iodo-1H-indol-3-yl)-cyclopentanone (325 mg, 1.0 mMol) as starting material, 3-(5-iodo-1H-indol-3-yl)-cyclopentyl-dimethylamine (330 mg, 93%) was obtained. $^1$H NMR (400 MHz, d4-MeOH) δ ppm 1.76 (m, 3 H) 2.12 (m, 3 H) 2.43 (2s, 6 H) 2.97 (m, 1 H) 3.32 (m, 1 H) 7.02 (2s, 1 H) 7.13 (2s, 1 H) 7.31 (2t, J=1.71 Hz, 1 H) 7.86 (2d, J=1.22 Hz, 1 H). LCMS (XTERRA C18 S5 4.6×50 mm) $t_R$, 1.383 min., MH$^+$ 355.21.

Example 27

3-(6-Fluoro-1H-indol-3-yl)-cyclopentyl-dimethylamine

Compound 42

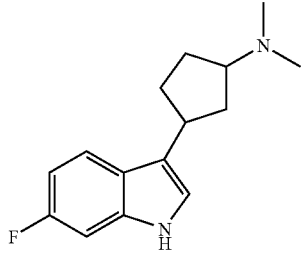

By the method of Example 21, using 3-(6-fluoro-1H-indol-3-yl)-cyclopentanone (217 mg, 1.0 mMol) as starting material, 3-(6-fluoro-1H-indol-3-yl)-cyclopentyl-dimethylamine (135 mg, 55%) was obtained. $^1$H NMR (400 MHz, d4MeOH) δ ppm 1.77 (m, 3 H) 2.15 (m, 3 H) 2.49 (s, 6 H) 3.10 (m, 1 H) 3.38 (m, 1 H) 6.75 (m, 1 H) 7.00 (m, 2 H) 7.47 (ddd, J=8.68, 5.75, 5.62 Hz, 1 H). LCMS (XTERRA C18 S5 4.6×50 mm) $t_R$, 1.103 min., MH$^+$ 247.29.

Example 28

3-(6-Chloro-1H-indol-3-yl)-cyclopentyl-dimethylamine

Compound 43

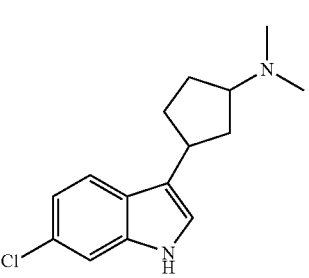

By the method of Example 21, using 3-(6-chloro-1H-indol-3-yl)-cyclopentanone (234 mg, 1.0 mMol) as starting material, 3-(6-chloro-1H-indol-3-yl)-cyclopentyl-dimethylamine (227 mg, 86%) was obtained. $^1$H NMR (400 MHz, d4MeOH) δ ppm 1.74 (m, 3 H) 2.10 (m, 3 H) 2.35 (s, 6 H) 2.83 (m, 1 H) 3.33 (m, 1 H) 6.93 (dt, J=8.50, 2.35 Hz, 1 H) 7.03 (d, J=13.69 Hz, 1 H) 7.29 (d, J=1.47 Hz, 1 H) 7.48 (m, 1 H). LCMS (XTERRA C18 S5 4.6×50 mm) $t_R$, 1.273 min., MH$^+$ 263.24.

Example 29

3-(6-Bromo-1H-indol-3-yl)-cyclopentyl-dimethylamine

Compound 44

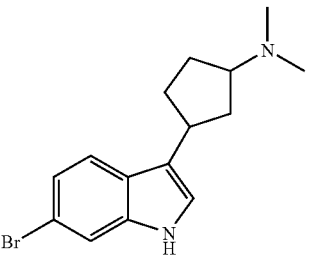

By the method of Example 21, using 3-(6-bromo-1H-indol-3-yl)-cyclopentanone (278 mg, 1.0 mMol) as starting material, 3-(6-bromo-1H-indol-3-yl)-cyclopentyl-dimethylamine (280 mg, 91%) was obtained. $^1$H NMR (400 MHz, d4MeOH) δ ppm 1.72 (m, 3 H) 2.14 (m, 3 H) 2.28 (d, J=4.40 Hz, 6 H) 2.75 (m, 1 H) 3.33 (m, 1 H) 7.01 (dd, J=14.18, 0.73 Hz, 1 H) 7.06 (ddd, J=8.50, 2.87, 1.83 Hz, 1 H) 7.44 (m, 2 H). LCMS (XTERRA C18 S5 4.6×50 mm) $t_R$, 1.330 min., MH$^+$ 307.21.

Example 30

3-(7-Fluoro-1H-indol-3-yl)-cyclopentyl-dimethyl-amine

Compound 45

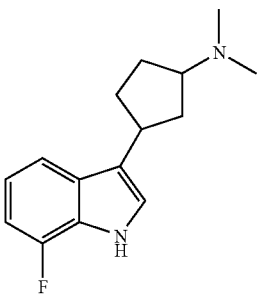

By the method of Compound 3, using 3-(7-fluoro-1H-indol-3-yl)-cyclopentanone (217 mg, 1.0 mMol) as starting material, 3-(7-fluoro-1H-indol-3-yl)-cyclopentyl-dimethylamine (144 mg, 59%) was obtained. $^1$H NMR (400 MHz, d4MeOH) δ ppm 1.74 (m, 3 H) 2.17 (m, 3 H) 2.34 (d, J=2.20 Hz, 6 H) 2.84 (m, 1 H) 3.34 (m, 1 H) 6.77 (dd, J=11.13, 8.19 Hz, 1 H) 6.90 (m, J=10.39, 5.07, 4.83, 2.45 Hz, 1 H) 7.05 (d, J=15.16 Hz, 1 H) 7.33 (t, J=7.70 Hz, 1 H). LCMS (XTERRA C18 S5 4.6×50 mm) $t_R$, 1.130 min., MH$^+$ 247.29.

Example 31

3-(7-Chloro-1H-indol-3-yl)-cyclopentyl-dimethyl-amine

Compound 46

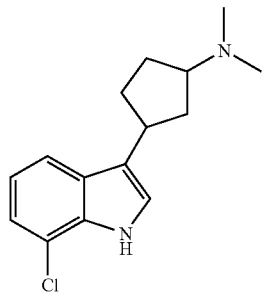

By the method of Example 21, using 3-(7-chloro-1H-indol-3-yl)-cyclopentanone (234 mg, 1.0 mMol) as starting material, 3-(7-chloro-1H-indol-3-yl)-cyclopentyl-dimethylamine (238 mg, 90%) was obtained. $^1$H NMR (400 MHz, d4MeOH) δ ppm 1.74 (m, 3 H) 2.17 (m, 3 H) 2.34 (d, J=1.71 Hz, 6 H) 2.86 (m, 1 H) 3.35 (m, 1 H) 6.94 (td, J=7.83, 2.45 Hz, 1 H) 7.07 (td, J=3.18, 1.22 Hz, 1 H) 7.11 (s, 1 H) 7.48 (td, J=7.46, 0.73 Hz, 1 H). LCMS (XTERRA C18 S5 4.6×50 mm) $t_R$, 1.273 min., MH$^+$ 263.24.

Example 32

3-(7-Bromo-1H-indol-3-yl)-cyclopentyl-dimethyl-amine

Compound 47

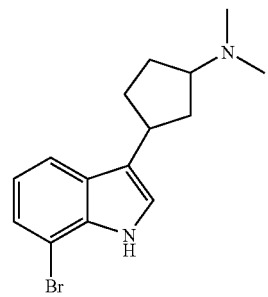

By the method of Example 21, using 3-(7-bromo-1H-indol-3-yl)-cyclopentanone (278 mg, 1.0 mMol) as starting material, 3-(7-bromo-1H-indol-3-yl)-cyclopentyl-dimethylamine (286 mg, 93%) was obtained. $^1$H NMR (400 MHz, d4MeOH) δ ppm 1.75 (m, 3 H) 2.17 (m, 3 H) 2.34 (d, J=1.96 Hz, 6 H) 2.85 (m, 1 H) 3.36 (m, 1 H) 6.89 (td, J=7.70, 2.20 Hz, 1 H) 7.07 and 7.11 (2s, 1 H) 7.22 (d, J=7.58 Hz, 1 H) 7.52 (td, J=7.34, 0.73 Hz, 1 H). LCMS (XTERRA C18 S5 4.6×50 mm) $t_R$, 1.303 min., MH$^+$ 307.21.

Example 33

(1S,3R)-3-(3-Dimethylaminocyclopentyl)-1H-indole-5-carbonitrile

Compound 48

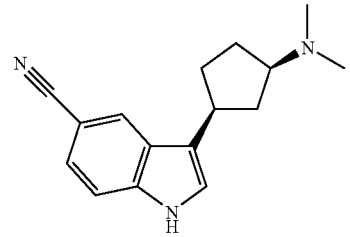

and (1S,3S)-3-(3-Dimethylaminocyclopentyl)-1H-indole-5-carbonitrile

Compound 49

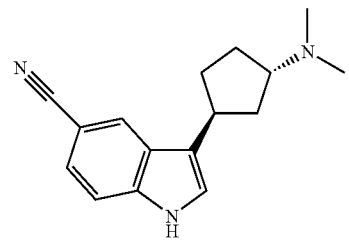

(1S)-3-(3-oxocyclopentyl)-1H-indole-5-carbonitrile (112 mg, 0.5 mMol) and dimethylamine (2.0 M solution in THF, 2.5 mL, 5.0 mMol) were dissolved in ethanol (2 mL). After stirring for 15 min, sodium triacetoxyborohydride (424 mg, 2.0 mMol) was added and the reaction continued for 2 h. The reaction was then diluted with water (5 mL) and made acidic (pH 3) with 6 M HCl. The reaction was then adjusted to pH 10 with sodium carbonate. It was extracted two times with ethyl acetate (50 mL) and the extracts were dried over sodium sulfate, concentrated in vacuo, and dried under high vacuum to give (1S)-3-(3-dimethylaminocyclopentyl)-1H-indole-5-carbonitrile (125 mg, 100%) as a cis/trans diastereomeric mixture. $^1$H NMR (500 MHz, d4-MeOH) δ 8.02 (0.7 H s), 7.99 (0.3 H, s), 7.46 (0.3 H, s), 7.44 (0.7 H, s), 7.35 (1 H, dd, J=8.24 1.53), 7.24 (0.7 H, s), 7.20 (0.3 H, s), 3.49 (0.3 H, m), 3.36 (0.7 H, m), 2.83 (0.2 H, m), 2.75 (0.8 H, m), 2.39 (1 H, m), 2.31 (6 H, s), 2.21 (1 H, m), 2.05 (1 H, m), 1.80 (2 H, m), 1.66 (1 H, m).

The (3R)- and (3S)-diastereomers of (1S)-3-(3-dimethylaminocyclopentyl)-1H-indole-5-carbonitrile were resolved by chiral HPLC on a Chiral Technologies Chiralpak AD column (20μ, 50×500 mm) with a mobile phase of 10% ethanol in hexane-0.1% diethylamine at a flow rate of 75 mL/min. Analytical HPLC retention times refer to the following analytical chiral HPLC method: Chiralpak AD column, 4.6×250 mm with 10 μm packing. Solvents: 10% Ethanol/hexane (0.10% diethyl amine added in hexane as modifier). Flow: 1 mL/min for 20 min. UV detector at 280 nm. Loop volume: 20 μL. Injection load: 20 μL of a 1 mg/mL solution in ethanol.

Compound 48: (1S,3R)-3-(3-Dimethylaminocyclopentyl)-1H-indole-5-carbonitrile. $^1$H NMR (500 MHz, d4-MeOH) δ 8.03 (1 H, d, J=0.92), 7.46 (1 H, d, J=8.55), 7.36 (1 H, dd, J=8.24 1.53), 7.25 (1 H, s), 3.39 (1 H, m), 2.81 (1 H, m), 2.42 (1 H, m), 2.35 (6 H, s), 2.22 (1 H, m), 2.08 (1 H, m), 1.86 (1 H, m), 1.77 (1 H, m), 1.67 (1 H, m). $[α]^{25}$ +12.95 (589 nm, c 1.58 mg/mL, EtOH). Analytical HPLC retention time 13 min.

Compound 49: (1S,3S)-3-(3-Dimethylaminocyclopentyl)-1H-indole-5-carbonitrile. $^1$H NMR (500 MHz, d4-MeOH) δ 7.99 (1 H, s), 7.45 (1 H, d, J=8.54), 7.36 (1 H, dd, J=8.24 1.52), 7.21 (1 H, s), 3.49 (1 H, m), 2.85 (1 H, m), 2.32 (6 H, s), 2.25 (1 H, m), 2.12 (2 H, m), 1.99 (1 H, m), 1.80 (1 H, m), 1.66 (1 H, m). $[α]^{25}$ −26.50 (589 nm, c 1.58 mg/mL, EtOH). Analytical HPLC retention time 8.4 min.

Example 34

(1R,3S)-3-(3-Dimethylaminocyclopentyl)-1H-indole-5-carbonitrile

Compound 50

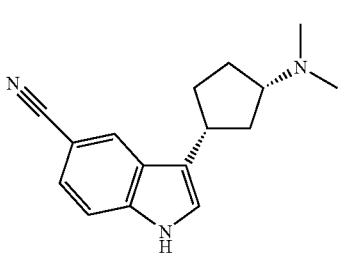

and (1R,3R)-3-(3-Dimethylaminocyclopentyl)-1H-indole-5-carbonitrile

Compound 51

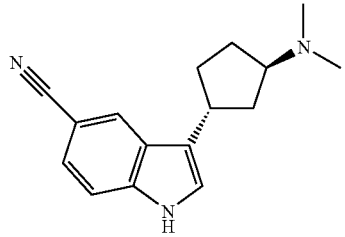

(1R)-3-(3-Oxocyclopentyl)-1H-indole-5-carbonitrile was reacted by the procedure used in Example 33, to give (1R)-3-(3-dimethylaminocyclopentyl)-1H-indole-5-carbonitrile (125 mg, 100%) as a cis/trans diastereomeric mixture. Yield: $^1$H NMR (500 MHz, d4-MeOH) δ 8.02 (0.7 H s), 7.99 (0.3 H, s), 7.46 (0.3 H, s), 7.44 (0.7 H, s), 7.35 (1 H, dd, J=8.24 1.53), 7.24 (0.7 H, s), 7.20 (0.3 H, s), 3.49 (0.3 H, m), 3.36 (0.7 H, m), 2.83 (0.2 H, m), 2.75 (0.8 H, m), 2.39 (1 H, m), 2.31 (6 H, s), 2.21 (1 H, m), 2.05 (1 H, m), 1.80 (2 H, m), 1.66 (1 H, m).

The (3S)- and (3R)-diastereomers of (1R)-3-(3-dimethylaminocyclopentyl)-1H-indole-5-carbonitrile were separated by the method given in Example 33. Analytical HPLC retention times refer to the method give in Example 33.

Compound 50: (1R,3S)-3-(3-Dimethylaminocyclopentyl)-1H-indole-5-carbonitrile. $^1$H δ (500 MHz, d4-MeOH) 8.03 (1 H, d, J=0.92), 7.46 (1 H, d, J=8.55), 7.36 (1 H, dd, J=8.24, 1.53), 7.25 (1 H, s), 3.38 (1 H, m), 2.86 (1 H, m), 2.43 (1 H, m), 2.38 (6 H, s), 2.23 (1 H, m), 2.09 (1 H, m), 1.86 (1 H, m), 1.78 (1 H, m), 1.68 (1 H, m). $[α]^{25}$ −8.12 (589 nm, c 1.71 mg/mL, EtOH). Analytical HPLC retention time 9.7 min.

Compound 51: (1R,3R)-3-(3-Dimethylaminocyclopentyl)-1H-indole-5-carbonitrile. $^1$H NMR (500 MHz, d4-MeOH) δ 8.01 (1 H, s), 7.47 (1 H, d, J=8.24), 7.37 (1 H, dd, J=8.24 1.52), 7.23 (1 H, s), 3.53 (1 H, m), 3.10 (1 H, m), 2.47 (6 H, s), 2.29 (1 H, m), 2.19 (2 H, m), 2.07 (1 H, m), 1.84 (1 H, m), 1.73 (1 H, m). $[α]^{25}$ +13.99 (589 nm, c 1.5 mg/mL, EtOH). Analytical HPLC retention time 8.6 min.

Example 35

(1S,3S)-3-(5-Fluoro-1H-indol-3-yl)-cyclopentyl-dimethylamine

Compound 52

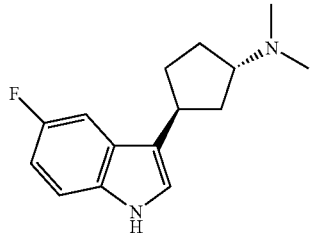

and (1R,3S)-3-(5-Fluoro-1H-indol-3-yl)-cyclopentyl-dimethylamine

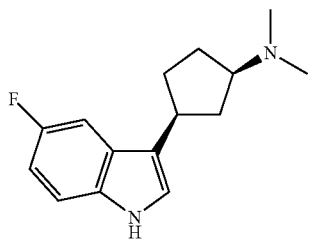

Compound 53

A solution of (3S)-3-(5-fluoro-1H-indol-3-yl)-cyclopentanone (290 mg, 1.34 mMol), dimethylamine (2.0 M solution in THF, 6.7 mL, 13.4 mMol) in ethanol (10 mL) was stirred for 15 min. Sodium triacetoxyborohydride (1.1 g, 5.4 mMol) was added and the reaction stirred for 1 h. The reaction was extracted three times with ethyl acetate/aqueous sodium bicarbonate solution. The ethyl acetate extracts were dried over magnesium sulfate and concentrated in vacuo to give (3S)-3-(5-fluoro-1H-indol-3-yl)-cyclopentyl-dimethylamine (400 mg, 100%) as a cis/trans diastereomeric mixture. The diastereomeric mixture was separated by preparative chiral HPLC using a Chiralpak AD column (50×500 mm with 20 μm packing) and 10% ethanol/hexane (0.1% diethylamine added in hexane as modifier) as the eluent at a flow rate of 60 mL/min for 50 min. The UV detector was set at 280 nm, the injection loop volume was 10 mL, and the injection load was 35–165 mg in a ethanol/hexane (1:1) solution.

Compound 52: (1S,3S)-3-(5-Fluoro-1H-indol-3-yl)-cyclopentyl-dimethylamine. $^1$H NMR (MeOH-d4): δ 7.28 (dd, J=8.7, 4.5 Hz, 1H), 7.22 (dd, J=10.2, 2.4 Hz, 1H), 7.14 (s, 1H), 6.86 (dt, J=2.4 Hz, 1H), 3.68 (t, 1H), 3.55 (m, 1H), 2.84 (s, 6H), 2.28 (m, 4H), and 1.88 (m, 2H). FIMS: m/z 247.4 (M+H)$^+$; m/z 245.4 (M−H)$^-$. [α]$^{25}$ −13.54 (589 nm, c 3.07 mg/mL, EtOH). >97% purity (reverse-phase HPLC); >99% purity with >99% ee (Chiralpak AD, 10% ethanol, 90% hexane (0.1% diethylamine), 0.5 mL/min, $R_t$=12.1 min)

Compound 53: (1R,3S)-3-(5-Fluoro-1H-indol-3-yl)-cyclopentyl-dimethylamine. $^1$H NMR (MeOH-d4): δ 7.27 (dd, J=9.0, 4.5 Hz, 1H), 7.24 (dd, J=8.7, 4.2 Hz, 1H), 7.21 (s, 1H), 6.86 (dt, J=9.3, 2.4 Hz, 1H), 3.35 (m, 1H), 3.18 (m, 1H), 2.58 (s, 6H), 2.47 (m, 1H), 2.18 (m, 2H), 1.86 (m, 2H), and 1.75 (q, J=10.5 Hz, 1H). FIMS: m/z 247.4 (M+H)$^+$; m/z 245.4 (M−H)$^-$. [α]$^{25}$ +2.54 (589 nm, c 2.79 mg/mL, EtOH). >99% purity (reverse-phase HPLC); >99% purity with >98% ee (Chiralpak AD, 10% ethanol, 90% hexane (0.1% diethylamine), 0.5 mL/min, $R_t$=15.7 min)

Example 36

(1R,3R)-3-(5-Fluoro-1H-indol-3-yl)-cyclopentyl-dimethylamine

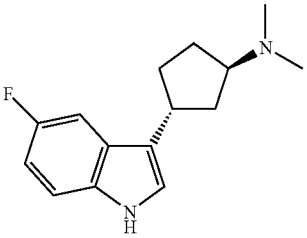

Compound 54 and (1S,3R)-3-(5-Fluoro-1H-indol-3-yl)-cyclopentyl-dimethylamine

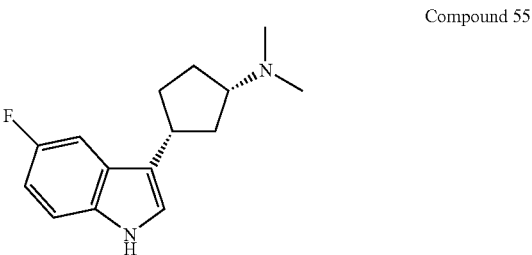

Compound 55

Similarly, (3R)-3-(5-fluoro-1H-indol-3-yl)-cyclopentanone was reacted by the method in Example 35 on a 0.92 mMol scale to give 240 mg (100%) of (3R)-3-(5-fluoro-1H-indol-3-yl)-cyclopentyl-dimethylamine as a cis/trans diastereomeric mixture. The diastereomeric mixture was separated by preparative chiral HPLC using a Chiralpak AD column (50×500 mm with 20 μm packing) and 10% ethanol/hexane (0.1% diethylamine added in hexane as modifier) as the eluent at a flow rate of 60 mL/min for 50 min. The UV detector was set at 280 nm, the injection loop volume was 10 mL, and the injection load was 35–165 mg in a ethanol/hexane (1:1) solution.

Compound 54: (1R,3R)-3-(5-Fluoro-1H-indol-3-yl)-cyclopentyl-dimethylamine. $^1$H NMR (MeOH-d4): δ 7.27 (dd, J=8.7, 4.5 Hz, 1H), 7.22 (dd, J=9.9, 2.4 Hz, 1H), 7.11 (s, 1H), 6.84 (dt, J=9.0, 2.4 Hz, 1H), 3.49 (t, 1H), 3.31 (m, 1H), 2.61 (s, 6H), 2.24 (m, 2H), 2.19 (q, J=15.3, 6.9 Hz, 2 H), and 1.80 (m, 2H). FIMS: m/z 247.4 (M+H)$^+$; m/z 245.4 (M−H)$^-$. [α]$^{25}$ +14.03 (589 nm, c 1.71 mg/mL, EtOH). >89% purity (reverse-phase HPLC); >99% purity with >99% ee (Chiralpak AD, 10% ethanol, 90% hexane (0.1% diethylamine), 0.5 mL/min, $R_t$=13.0 min)

Compound 55: (1S,3R)-3-(5-Fluoro-1H-indol-3-yl)-cyclopentyl-dimethylamine. $^1$H NMR (MeOH-d4): δ 7.26 (dd, J=8.7, 4.5 Hz, 1H), 7.21 (dd, J=9.9, 2.4 Hz, 1H), 7.11 (s, 1H), 6.83 (dt, J=2.4 Hz, 1H), 3.31 (m, 1H), 2.90 (m, 1H), 2.41 (s, 6H), 2.39 (m, 1H), 2.20 (m, 1H), 2.10 (m, 1H), 1.80 (m, 2 H), and 1.68 (q, J=10.5 Hz, 1H). FIMS: m/z 248.3 (M+H)$^+$; m/z 245.4 (M−H)$^-$. [α]$^{25}$ −12.32 (589 nm, c 1.93 mg/mL, EtOH). >97% purity (reverse-phase HPLC); >98%

Example 37

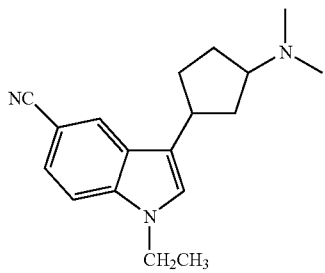

(1S,3R)-3-(3-Dimethylamino-cyclopentyl)-1-ethyl-1H-indole-5-carbonitrile

Compound 56

(1S,3S)-3-(3-Dimethylamino-cyclopentyl)-1-ethyl-1H-indole-5-carbonitrile

Compound 57

(1R,3S)-3-(3-Dimethylamino-cyclopentyl)-1-ethyl-1H-indole-5-carbonitrile

Compound 58

(1R,3R)-3-(3-Dimethylamino-cyclopentyl)-1-ethyl-1H-indole-5-carbonitrile

Compound 59

A solution of (1S,3R)-3-dimethylaminocyclopentyl)-1H-indole-5-carbonitrile (350 mg, 1.4 mMol) and potassium t-butoxide (233 mg, 2.1 mMol) in anhydrous THF (20 mL) was stirred under nitrogen for 30 m. Diethylsulfate (320 mg, 2.1 mMol) was added and the solution was stirred for 1.5 h. The reaction was poured into H$_2$O (250 mL) and extracted with ethyl acetate. The organic extracts were washed with brine, dried over sodium sulfate, and concentrated in vacuo. The residue was purified by chromatography on silica gel (10 g) with 3% 2M NH$_3$/methanol in CH$_2$Cl$_2$. The pure product fractions were concentrated and dried in vacuo to give (1S,3R)-3-(3-dimethylamino-cyclopentyl)-1-ethyl-1H-indole-5-carbonitrile (Compound 56) (208 mg, 53%). $^1$H NMR (500 MHz, d4-MeOH) δ 8.02 (1 H s), 7.51 (1 H, d, J=8.55), 7.40 (1 H, dd, J=8.55 1.53), 7.28 (1 H, s), 4.21 (2 H, q, J=7.33), 3.36 (1 H, m), 2.76 (1 H, m), 2.40 (1 H, m), 2.32 (6 H, s), 2.21 (1 H, m), 2.06 (1 H, m), 1.83 (1 H, m), 1.75 (1 H, m), 1.65 (1 H, dd, J=21.97, 11.59), 1.41 (3 H, t, J=7.33). LCMS (XTERRA C18 S5 4.6×50 mm) t$_R$, 1.253 min., MH$^+$ 282.29.

The following compounds were prepared using procedures similar to the above:

Compound 57: (1S, 3S)-3-(3-Dimethylamino-cyclopentyl)-1-ethyl-1H-indole-5-carbonitrile was prepared on a 0.071 mMol scale to yield 4 mg (20%). $^1$H NMR (500 MHz, d4-MeOH) δ 7.99 (1 H s), 7.51 (1 H, d, J=8.55), 7.41 (1 H, dd, J=8.55 1.53), 7.24 (1 H, s), 4.21 (2 H, q, J=7.33), 3.48 (1 H, m), 2.83 (1 H, m), 2.31 (6 H, s), 2.25 (1 H, m), 2.11 (2 H, m), 1.98 (1 H, m), 1.79 (1 H, m), 1.66 (1 H, m), 1.41 (3 H, t, J=7.33). LCMS (XTERRA C18 S5 4.6×50 mm) t$_R$, 1.253 min., MH$^+$ 282.29.

Compound 58: (1R,3S)-3-(3-Dimethylamino-cyclopentyl)-1-ethyl-1H-indole-5-carbonitrile was prepared on a 0.17 mMol scale to yield 26 mg (54%). $^1$H NMR (500 MHz, d4-MeOH) δ 8.02 (1 H s), 7.50 (1 H, d, J=8.55), 7.40 (1 H, dd, J=8.55 1.53), 7.27 (1 H, s), 4.21 (2 H, q, J=7.33), 3.36 (1 H, m), 2.74 (1 H, m), 2.39 (1 H, m), 2.31 (6 H, s), 2.21 (1 H, m), 2.05 (1 H, m), 1.83 (1 H, m), 1.75 (1 H, m), 1.64 (1 H, dd, J=22.28, 11.59), 1.41 (3 H, t, J=7.33). LCMS (XTERRA C18 S5 4.6×50 mm) t$_R$, 1.257 min., MH$^+$ 282.29.

Compound 59: (1R,3R)-3-(3-Dimethylamino-cyclopentyl)-1-ethyl-1H-indole-5-carbonitrile was prepared on a 0.065 mMol scale to yield 7 mg (38%). $^1$H NMR (500 MHz, d4-MeOH) δ 7.99 (1 H s), 7.51 (1 H, d, J=8.55), 7.41 (1 H, dd, J=8.55 1.53), 7.24 (1 H, s), 4.21 (2 H, q, J=7.33), 3.48 (1 H, m), 2.82 (1 H, m), 2.30 (6 H, s), 2.25 (1 H, m), 2.12 (2 H, m), 1.98 (1 H, m), 1.78 (1 H, m), 1.65 (1 H, m), 1.41 (3 H, t, J=7.33). LCMS (XTERRA C18 S5 4.6×50 mm) t$_R$, 1.257 min., MH$^+$ 282.29.

Example 38

Alternate procedure for the preparation of racemic Cis-3-(3-dimethylaminocyclopentyl)-1H-indole-5-carbonitrile

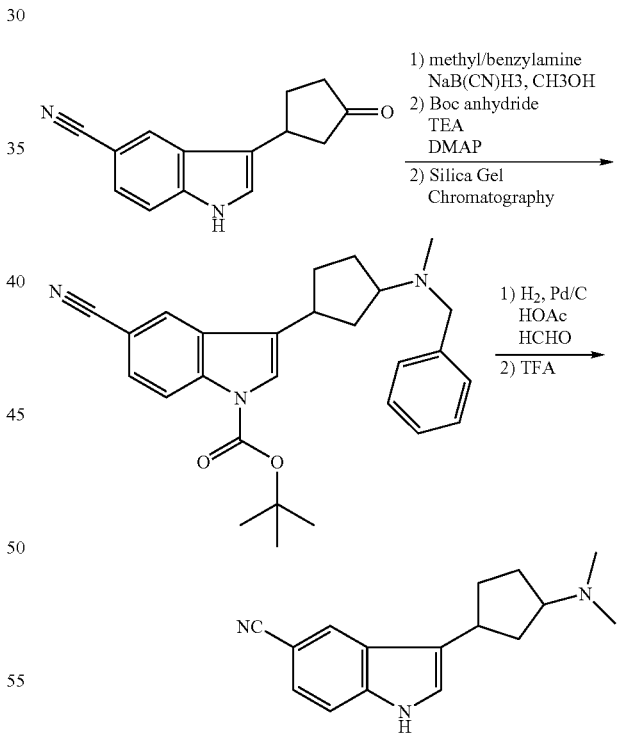

Sodium cyanoborohydride (2.8 g, 45 mMol) was added to a solution of racemic 3-(3-oxocyclopentyl)-1H-indole-5-carbonitrile (5 g, 22.3 mMol) and N-methylbenzylamine (7.25 mL, 56 mMol) in methanol (200 mL). The resulting mixture was stirred for 16 hr and then concentrated in vacuo. The residue was dissolved in ethyl acetate and washed with aqueous sodium bicarbonate, then with brine, and dried over magnesium sulfate. The ethyl acetate solution was concentrated in vacuo to give the crude product which was dissolved in methylene chloride (150 mL). Di-tert-butyl-dicarbonate (21 g, 96 mMol), triethylamine (13 mL, 94 mMol), 4-dimethylaminopyridine (200 mg, 1.64 mMol) were added to the solution. The resulting mixture was stirred for 2 h. The reaction mixture was washed with aqueous sodium bicarbonate. The aqueous layer was extracted with methylene chloride (2×50 mL). The methylene chloride extracts were combined, washed with aqueous sodium bicarbonate, and with brine, dried over magnesium sulfate. The methylene chloride solution was concentrated in vacuo to give the crude product as a mixture of cis/trans diastereomers. The mixture was separated by chromatography on silica gel using ethyl acetate/hexane (0–30%) to give cis-1-BOC-3-[3-(N-benzyl-N-methylamino)-cyclopentyl]-1H-indole-5-carbonitrile (5 g, 63%) and trans-1-BOC-3-[3-(N-benzyl-N-methylamino)-cyclopentyl]-1H-indole-5-carbonitrile (1 g, 13%) as evidenced by NOE NMR experiment. $^1$H NMR (500 MHz, CDCl$_3$) cis: δ 1.67 (s, 9H); 1.83 (m, 3H); 2.06 (m,1H); 2.18 (s, 3H); 2.20 (m, 1H); 2.40 (m,1H); 3.00 (m, 1H); 3.25 (m,1H); 3.56 (dd, 2H); 7.33 (m, 5H); 7.48 (s, 1H); 7.53 (d, 1H); 7.89 (s, 1H); 8.23 (d, 2H). M+1=430. trans: δ 1.66 (s, 9H); 1.76 (m, 2H); 1.97 (m,1H); 2.10 (m, 1H); 2.18 (s, 3H); 2.23 (m, 2H); 3.08 (m, 1H); 3.39 (m,1H); 3.55 (s, 2H); 7.32 (m, 5H); 7.43 (s, 1H); 7.55 (d, 1H); 7.87 (s, 1H); 8.20 (d, 2H). M+1=430.

A mixture of cis-1-BOC-3-[3-(N-benzyl-N-methylamino)-cyclopentyl]-1H-indole-5-carbonitrile (500 mg, 1.2 mMol), 10% palladium on carbon (200 mg), formaldehyde (1.2 mL of 30% aqueous, 12 mMol), and acetic acid (0.1 mL) in methylene chloride (10 mL) and methanol (20 mL) was stirred under hydrogen (balloon pressure) for 4 h. The mixture was filtered and the filtrate was concentrated in vacuo. The residue was dissolved in methylene chloride (10 mL) and trifluoroacetic acid (3 mL) and stirred for 18 h. The solution was concentrated in vacuo, and the residue was dissolved in ethyl acetate. The ethyl acetate solution was washed with aqueous NaHCO$_3$, and then brine, and dried over magnesium sulfate. The solution was concentrated to give the crude product which was purified by preparative HPLC to give cis-3-(3-dimethylaminocyclopentyl)-1H-indole-5-carbonitrile (120 mg, 40%).

Example 39

(1S)-3-(3-Amino-cyclopentyl)-1H-indole-5-carbonitrile

Compound 60

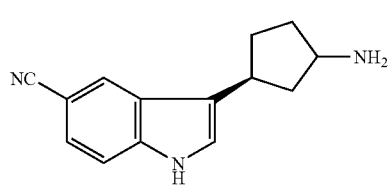

and (3S,3'S)-Bis-(3-(5-cyano-1H-indol-3-yl)cyclopentyl)amine

Compound 61

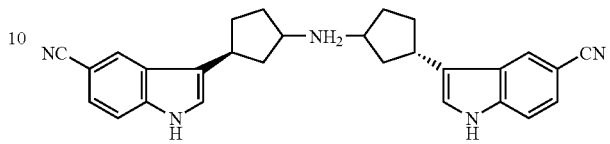

A mixture of the (1S)-3-(3-oxocyclopentyl)-1H-indole-5-carbonitrile (1.0 g, 4.5 mMol), ammonium acetate (5.5 g, 71 mMol), sodium cyanoborohydride (0.3 g, 4.76 mMol), and 4A molecular sieves (3 g) in 20 mL of methanol was stirred at room temperature overnight. Reaction was filtered and the filtrate was concentrated. The residue was partitioned between ethyl acetate/aqueous sodium bicarbonate. The organic layer was washed by aqueous sodium bicarbonate and brine, dried with MgSO$_4$, and concentrated to give the crude product (0.9 g) which was separated by preparative HPLC (Column: XTERRA 30×75 mm S5; Solvent A=10% methanol/90% H$_2$O/0.1% TFA, Solvent B=90% methanol/10% H$_2$O/0.1% TFA; Start 15% B, Final 100% B, Gradient time 8 min, Flow rate 30 mL/min).

Compound 60: (1S)-3-(3-Amino-cyclopentyl)-1H-indole-5-carbonitrile was the first to elute (149 mg, 15%) $^1$H NMR (400 MHz, d4-MeOH) δ 8.0 (1H, m), 7.42 (1 H, m), 7.32 (1 H, m), 7.17 (1 H, d), 3.55 (1 H, m), 1.53–2.18 (m, 6H). LCMS (XTERRA C18 S7 3.0×50 mm) $t_R$, 1.07 min., MH$^+$ 226.17.

Compound 61: (3S,3'S)-Bis-(3-(5-cyano-1H-indol-3-yl)cyclopentyl)amine eluted second (310 mg, 32%). $^1$H NMR (400 MHz, d4-MeOH) δ 8.0 (1 H, d), 7.43 (2 H, d), 7.35 (2 h, d), 7.20 (2 H, d), 3.51 (2 H, m), 1.6–2.6 (12 H, m). LCMS (XTERRA C18 S7 3.0×50 mm) $t_R$, 1.90 min., MH$^+$ 434.19.

Example 40

Serotonin Transporter Binding Assay

HEK-293 cells that stably express human serotonin transporters (HEK-hSERT cells) were grown at 37° C. in 5% CO$_2$ as a monolayer in medium consisting of EMEM supplemented with 10% fetal bovine serum and G418 sulfate (500 μg/mL). To prepare membranes for radioligand binding experiments, cells were rinsed twice with phosphate-buffered saline (138 mM NaCl, 4.1 mM KCl, 5.1 mM Na$_2$PO$_4$, 1.5 mM KH$_2$O$_4$, 11.1 mM glucose, pH 7.4). Cells were transferred from plates to polypropylene tubes (16×100 mm), centrifuged at 1,200×g for 5 min and were frozen at −80° C. until assay. Following centrifugation, pellets were resuspended by homogenization in buffer consisting of 50 mM Tris (pH 7.7 at 25° C.), 120 mM NaCl and 5 mM KCl and then centrifuged at 32,000×g for 10 min. Following centrifugation, supernatants were discarded and pellets were resuspended in buffer consisting of 50 mM Tris (pH 7.4 at 25° C.), 150 mM NaCl and 5 mM KCl. Membrane homogenates (200 μl/plate) were incubated with 1 nM [$^3$H]-citalopram (specific activity=85 Ci/mMol) and increasing concentrations of test compounds for 1 hr at 25° C. in a total volume of 250 μl. The assay buffer consisted of 50 mM Tris (pH 7.4 at 25° C.), 120 mM NaCl and 5 mM KCl (pH 7.4 with conc. HCl). Plates were incubated for 1 hr at 25° C., then filtered through 0.5% PEI treated Whatman GF/B filters using a Brandel cell harvester. Filters were washed three times with 3 mL of ice-cold tris wash buffer. Non-specific binding was defined with 10 µM fluoxetine. Amount of radioligand bound in the presence and absence of competitor was analyzed by plotting (−)log drug concentration versus the amount of radioligand specifically bound. The midpoint of the displacement curve ($IC_{50}$, nM), signifies the potency. $K_i$ values were calculated using the method of Cheng and Prusoff (1973).

Example 41

Norepinephrine Transporter Binding Assay

MDCK cells that stably express human norepinephrine transporters (HEK-hNET cells) were supplied by Receptor Biology, Inc. Pellets were resuspended by homogenization in buffer consisting of 50 mM Tris (pH 7.4 at 25° C.), 120 mM NaCl and 5 mM KCl. Membrane homogenates (200 µl/well, 8 ug protein) were incubated with 2.7 nM [$^3$H]-nisoxetine (specific activity=80 Ci/mMol) and increasing concentrations of test compounds for 1 hr at 4° C. in a total volume of 250 µl. The assay buffer consisted of 50 mM Tris (pH 7.4 at 25° C.), 120 mM NaCl and 5 mM KCl (pH 7.4 with conc. HCl). Plates were incubated for 1 hr at 4° C., then filtered through 0.5% PEI treated Whatman GF/B filters using a Brandel cell harvester. Filters were washed three times with 3 mL of ice-cold tris wash buffer. Non-specific binding was defined with 10 µM desipramine. Amount of radioligand bound in the presence and absence of competitor was analyzed by plotting (−)log drug concentration versus the amount of radioligand specifically bound. The midpoint of the displacement curve ($IC_{50}$, nM), signifies the potency. $K_i$ values were calculated using the method of Cheng and Prusoff (1973).

Compounds of the present invention demonstrate SERT binding and may be useful for the treatment of depression, anxiety disorders, premature ejaculation, chronic pain, obsessive-compulsive disorder, feeding disorders, premenstrual dysphoric disorder and panic disorders. Moreover, particular compounds of Formula I demonstrate no norepinephrine reuptake inhibition, and therefore should have a reduced probability of any cardiovascular liabilities associated with norepinephrine reuptake inhibition.

In the table below, binding results are denoted as follows:

| COMPOUND | NAME | STRUCTURE | SERT | NE Reuptake |
|---|---|---|---|---|
| 1 | 3-(3-Methylamino-cyclopentyl)-1H-indole-5-carbonitrile | 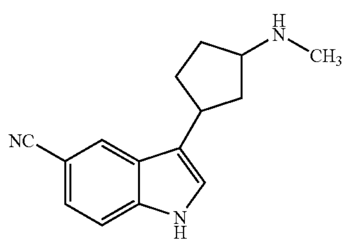 | B | E |
| 2 | 3-(3-Ethylamino-cyclopentyl)-1H-indole-5-carbonitrile | 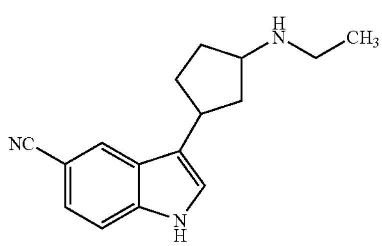 | B | E |
| 3 | 3-(3-Dimethylamino-cyclopentyl)-1H-indole-5-carbonitrile | 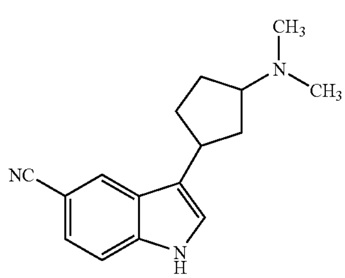 | A | E |

-continued

| COMPOUND | NAME | STRUCTURE | SERT | NE Reuptake |
|---|---|---|---|---|
| 4 | 3-[3-(Ethyl-methyl-amino)-cyclopentyl]-1H-indole-5-carbonitrile | 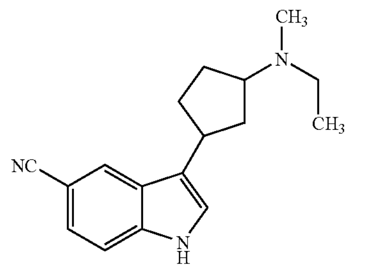 | B | E |
| 5 | 3-(3-Diethylamino-cyclopentyl)-1H-indole-5-carbonitrile | 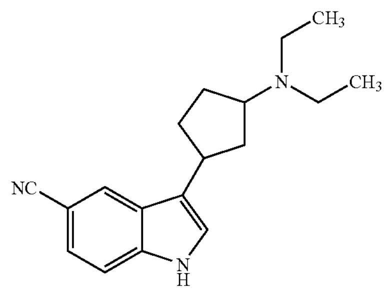 | B | E |
| 6 | 3-(3-Pyrrolidin-1-yl-cyclopentyl)-1H-indole-5-carbonitrile | 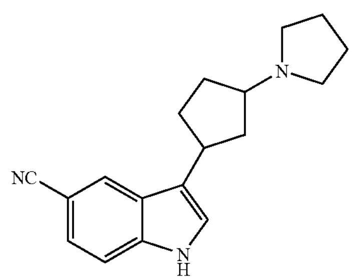 | B | E |
| 7 | 3-[3-(1,3-Dihydro-isoindol-2-yl)-cyclopentyl]-1H-indole-5-carbonitrile | 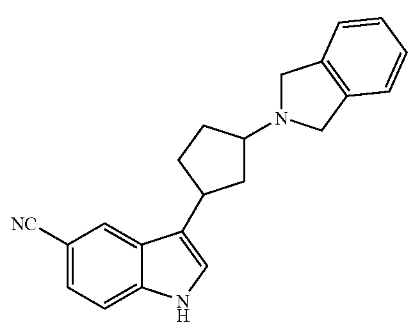 | B | E |
| 8 | 3-[3-(3,4-Dihydro-1H-isoquinolin-2-yl)-cyclopentyl]-1H-indole-5-carbonitrile | 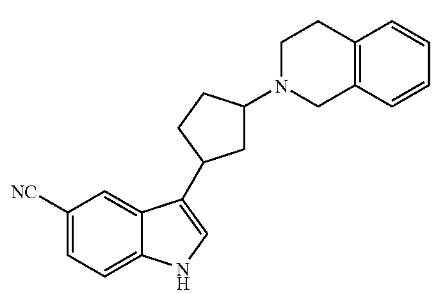 | B | D |

-continued

| COMPOUND | NAME | STRUCTURE | SERT | NE Reuptake |
|---|---|---|---|---|
| 9 | 3-(3-Phenethylamino-cyclopentyl)-1H-indole-5-carbonitrile | 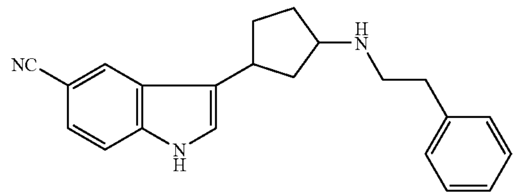 | B | D |
| 10 | 3-[3-(Methyl-phenethyl-amino)-cyclopentyl]-1H-indole-5-carbonitrile | 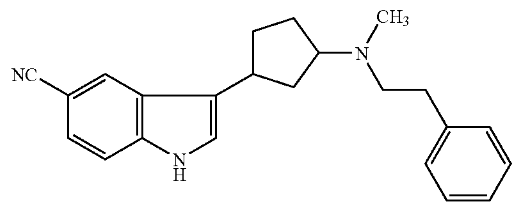 | B | D |
| 11 | 3-(3-Morpholin-4-yl-cyclopentyl)-1H-indole-5-carbonitrile | 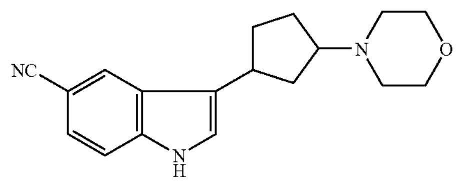 | A | E |
| 12 | 3-[3-(Benzyl-methyl-amino)-cyclopentyl]-1H-indole-5-carbonitrile | 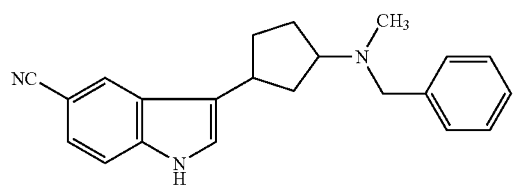 | B | D |
| 13 | 3-(3-Benzylamino-cyclopentyl)-1H-indole-5-carbonitrile | 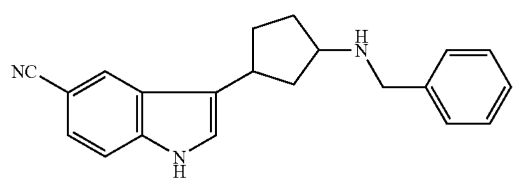 | B | D |
| 14 | 3-(3-Piperidin-1-yl-cyclopentyl)-1H-indole-5-carbonitrile | 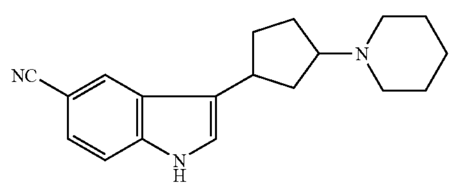 | A | E |
| 15 | 3-(3-Dipropylamino-cyclopentyl)-1H-indole-5-carbonitrile | 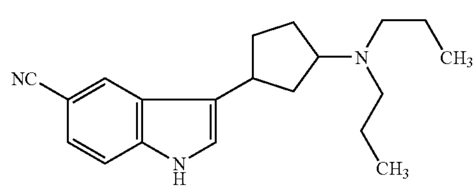 | B | E |
| 16 | 3-(3-Propylamino-cyclopentyl)-1H-indole-5-carbonitrile | 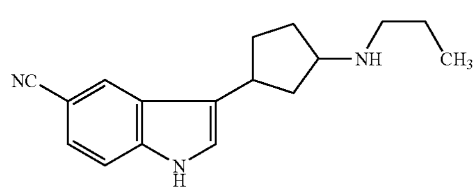 | A | E |

-continued

| COMPOUND | NAME | STRUCTURE | SERT | NE Reuptake |
|---|---|---|---|---|
| 17 | 1-Methyl-3-(3-methylamino-cyclopentyl)-1H-indole-5-carbonitrile | 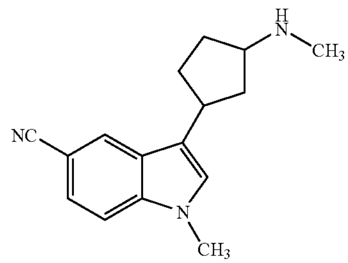 | B | E |
| 18 | 3-(3-Ethylamino-cyclopentyl)-1-methyl-1H-indole-5-carbonitrile | 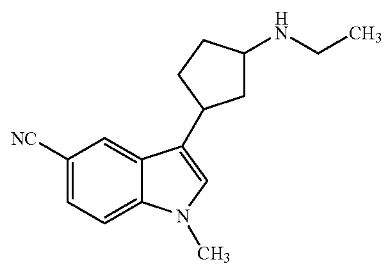 | A | E |
| 19 | 3-(3-Benzylamino-cyclopentyl)-1-methyl-1H-indole-5-carbonitrile | 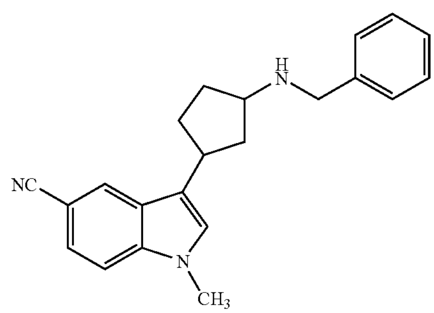 | B | D |
| 20 | 1-Methyl-3-(3-phenethylamino-cyclopentyl)-1H-indole-5-carbonitrile | 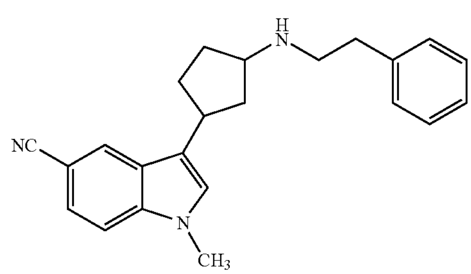 | B | D |
| 21 | 3-(3-Dimethylamino-cyclopentyl)-1-methyl-1H-indole-5-carbonitrile | 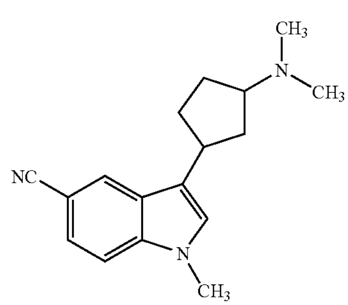 | B | E |

-continued
| COMPOUND | NAME | STRUCTURE | SERT | NE Reuptake |
|---|---|---|---|---|
| 22 | 3-[3-(Ethyl-methyl-amino)-cyclopentyl]-1-methyl-1H-indole-5-carbonitrile | 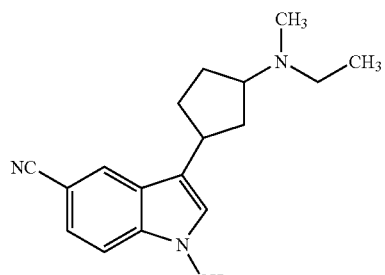 | B | E |
| 23 | 3-(3-Diethylamino-cyclopentyl)-1-methyl-1H-indole-5-carbonitrile | 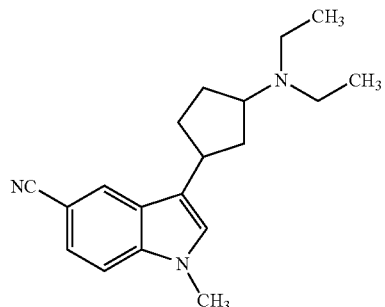 | A | E |
| 24 | 1-Methyl-3-(3-pyrrolidin-1-yl-cyclopentyl)-1H-indole-5-carbonitrile | 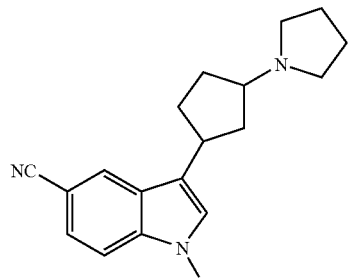 | B | E |
| 25 | 1-Methyl-3-(3-piperidin-1-yl-cyclopentyl)-1H-indole-5-carbonitrile | 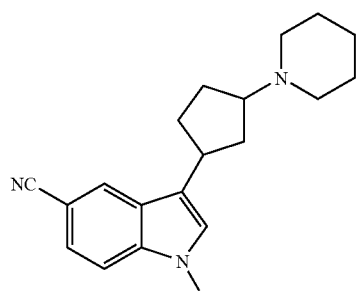 | A | E |
| 26 | 1-Methyl-3-(3-morpholin-4-yl-cyclopentyl)-1H-indole-5-carbonitrile | 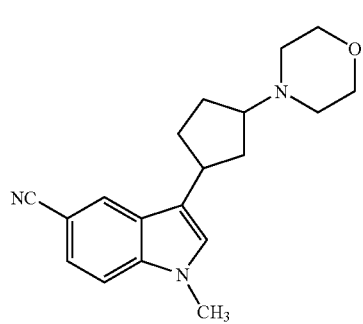 | A | E |

| COMPOUND | NAME | STRUCTURE | SERT | NE Reuptake |
|---|---|---|---|---|
| 27 | 3-[3-(Benzyl-methyl-amino)-cyclopentyl]-1-methyl-1H-indole-5-carbonitrile | 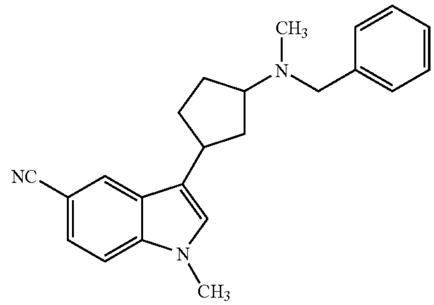 | A | E |
| 28 | 1-Methyl-3-[3-(methyl-phenethyl-amino)-cyclopentyl]-1H-indole-5-carbonitrile | 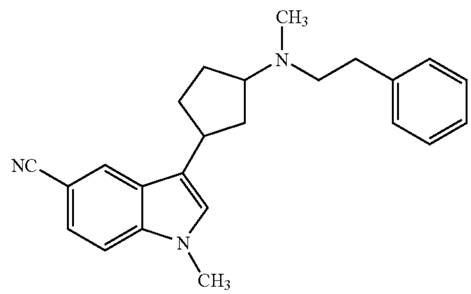 | B | D |
| 29 | 1-Methyl-3-(3-propylamino-cyclopentyl)-1H-indole-5-carbonitrile | 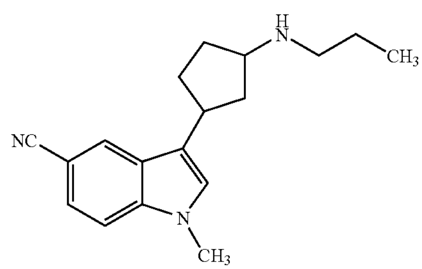 | A | E |
| 30 | 3-(3-Dipropylamino-cyclopentyl)-1-methyl-1H-indole-5-carbonitrile | 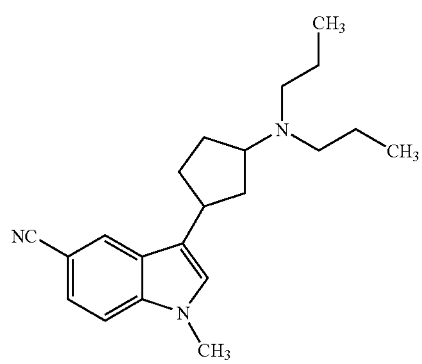 | A | E |
| 31 | 3-[3-(Benzyl-methyl-amino)-cyclopentyl]-1-ethyl-1H-indole-5-carbonitrile | 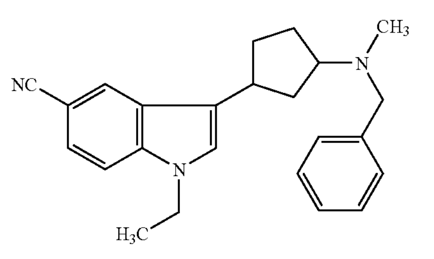 | B | E |

-continued

| COMPOUND | NAME | STRUCTURE | SERT | NE Reuptake |
|---|---|---|---|---|
| 32 | 3-(3-Dimethylamino-cyclopentyl)-1-ethyl-1H-indole-5-carbonitrile | 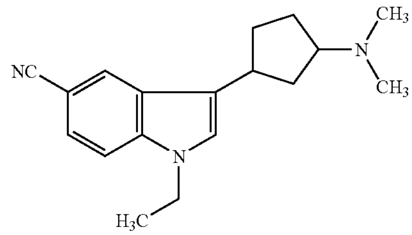 | A | E |
| 33 | 3-(5-Fluoro-1H-indol-3-yl)-cyclopentyl]-dimethyl-amine | 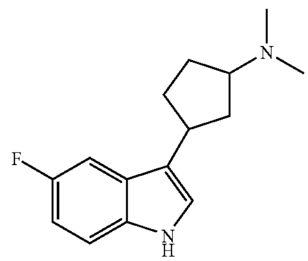 | A | E |
| 34 | Ethyl-[3-(5-fluoro-1H-indol-3-yl)cyclopentyl]-methyl-amine | 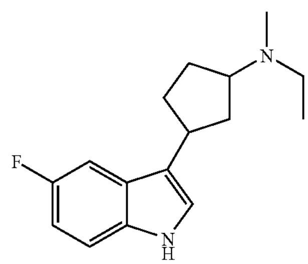 | B | E |
| 35 | Diethyl-[3-(5-fluoro-1H-indol-3-yl)-cyclopentyl]-amine | 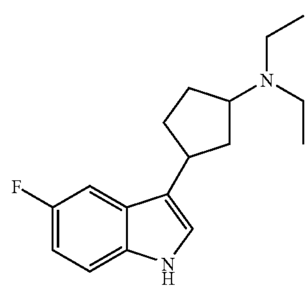 | 5 | E |
| 36 | 5-Fluoro-3-(3-pyridin-1-yl-cyclopentyl)-1H-indole | 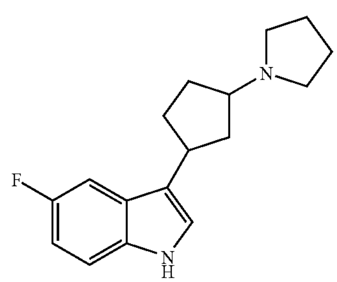 | B | E |

-continued

| COMPOUND | NAME | STRUCTURE | SERT | NE Reuptake |
|---|---|---|---|---|
| 37 | 3-(4-Fluoro-1H-indol-3-yl)-cyclopentyl-dimethyl-amine | 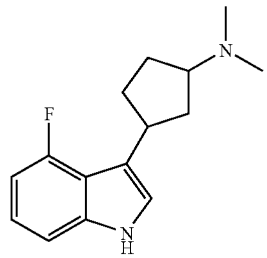 | C | Not tested |
| 38 | 3-(4-Bromo-1H-indol-3-yl)-cyclopentyl-dimethyl-amine | 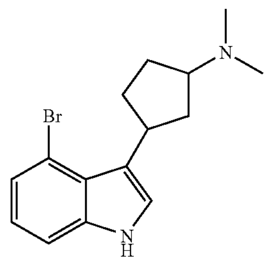 | B | Not tested |
| 39 | 3-(5-Chloro-1H-indol-3-yl)-cyclopentyl-dimethyl-amine | 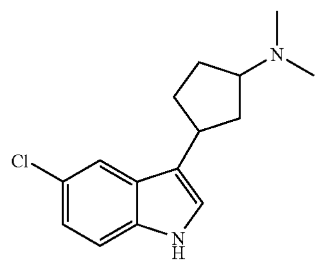 | B | Not tested |
| 40 | 3-(5-Bromo-1H-indol-3-yl)-cyclopentyl-dimethyl-amine | 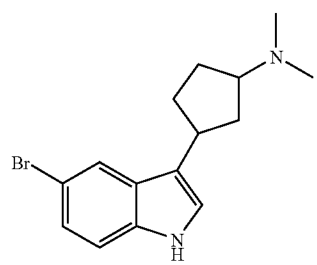 | B | Not tested |
| 41 | 3-(5-Iodo-1H-indol-3-yl)-cyclopentyl-dimethyl-amine | 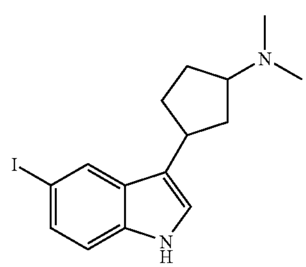 | C | Not tested |
| 42 | 3-(6-Fluoro-1H-indol-3-yl)-cyclopentyl-dimethyl-amine | 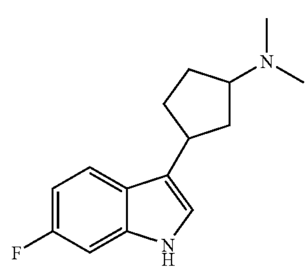 | B | Not tested |

| COMPOUND | NAME | STRUCTURE | SERT | NE Reuptake |
|---|---|---|---|---|
| 43 | 3-(6-Chloro-1H-indol-3-yl)-cyclopentyl-dimethyl-amine | 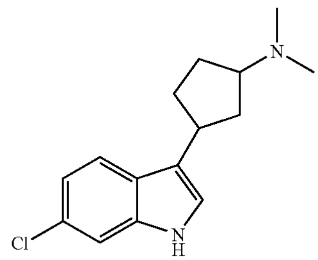 | B | Not tested |
| 44 | 3-(6-Bromo-1H-indol-3-yl)-cyclopentyl-dimethyl-amine | 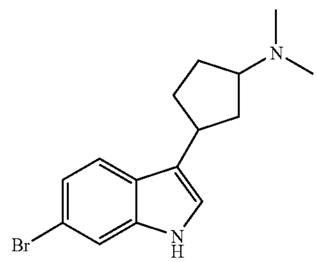 | B | Not tested |
| 45 | 3-(7-Fluoro-1H-indol-3-yl)-cyclopentyl-dimethyl-amine | 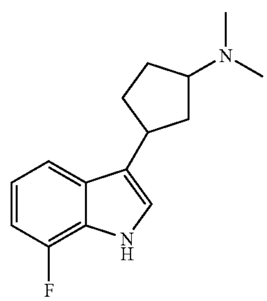 | B | Not tested |
| 46 | 3-(7-Chloro-1H-indol-3-yl)-cyclopentyl-dimethyl-amine | 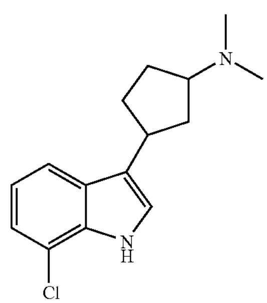 | A | Not tested |
| 47 | 3-(7-Bromo-1H-indol-3-yl)-cyclopentyl-dimethyl-amine | 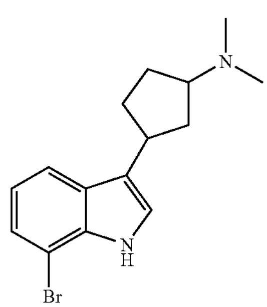 | B | Not tested |

-continued

| COMPOUND | NAME | STRUCTURE | SERT | NE Reuptake |
|---|---|---|---|---|
| 48 | (1S,3R)-3-(3-dimethylaminocyclopentyl)-1H-indole-5-carbonitrile | 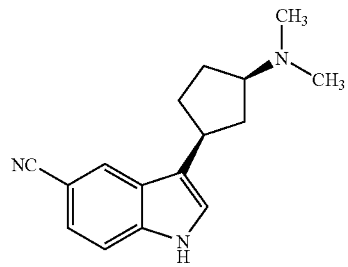 | A | E |
| 49 | (1S,3S)-3-(3-dimethylaminocyclopentyl)-1H-indole-5-carbonitrile | 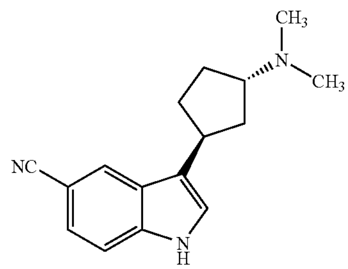 | A | E |
| 50 | (1R,3S)-3-(3-dimethylaminocyclopentyl)-1H-indole-5-carbonitrile | 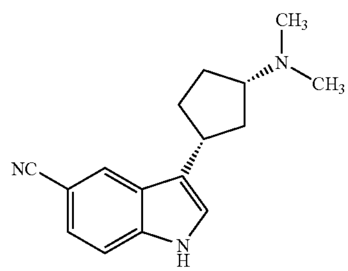 | A | E |
| 51 | (1R,3R)-3-(3-dimethylaminocyclopentyl)-1H-indole-5-carbonitrile | 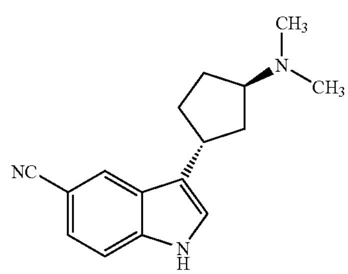 | A | E |
| 52 | (1S,3S)-3-(5-fluoro-1H-indol-3-yl)-cyclopentyl-dimethylamine | 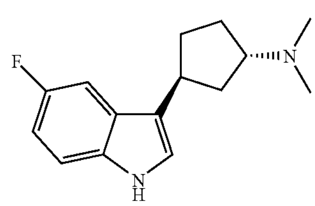 | B | E |
| 53 | (1R,3S)-3-(5-fluoro-1H-indol-3-yl)-cyclopentyl-dimethylamine | 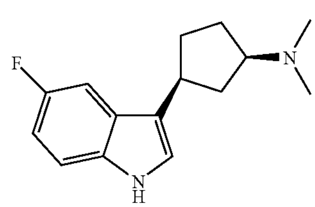 | A | E |

-continued

| COMPOUND | NAME | STRUCTURE | SERT | NE Reuptake |
|---|---|---|---|---|
| 54 | (1R,3R)-3-(5-fluoro-1H-indol-3-yl)-cyclopentyl-dimethylamine | 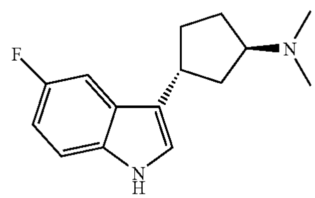 | B | E |
| 55 | (1S,3R)-3-(5-fluoro-1H-indol-3-yl)-cyclopentyl-dimethylamine | 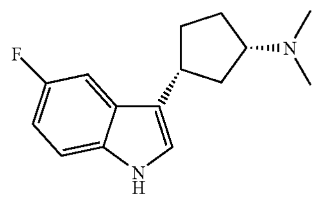 | B | E |
| 56 | (1S,3R)-3-(3-Dimethylamino-cyclopentyl)-1-ethyl-1H-indole-5-carbonitrile | 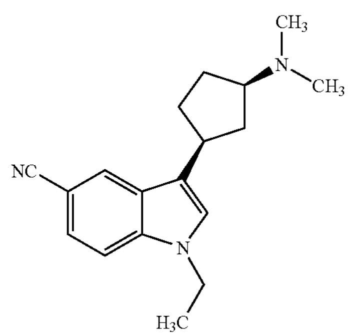 | A | E |
| 57 | (1S,3S)-3-(3-Dimethylamino-cyclopentyl)-1-ethyl-1H-indole-5-carbonitrile | 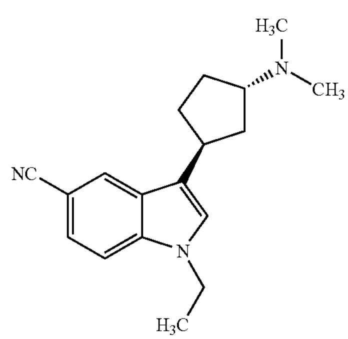 | B | E |
| 58 | (1R,3S)-3-(3-Dimethylamino-cyclopentyl)-1-ethyl-1H-indole-5-carbonitrile | 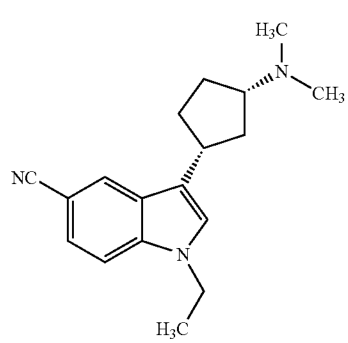 | A | E |

| COMPOUND | NAME | STRUCTURE | SERT | NE Reuptake |
|---|---|---|---|---|
| 59 | (1R,3R)-3-(3-Dimethylamino-cyclopentyl)-1-ethyl-1H-indole-5-carbonitrile | 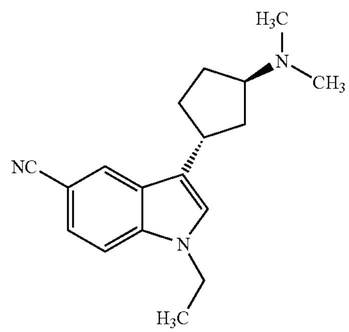 | B | E |
| 60 | (1S)-3-(3-Amino-cyclopentyl)-1H-indole-05-carbonitrile | 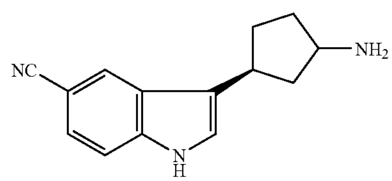 | C | Not tested |
| 61 | (3S,3'S)-bis-(3-(5-cyano-1H-indol-3-yl)cyclopentyl)amine | 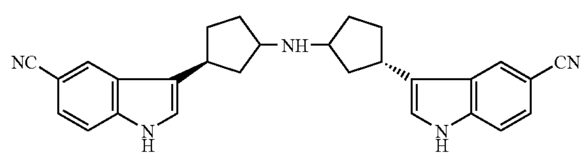 | B | Not tested |

A: Ki < 1 nM;
B: 1 nM < Ki < 10 nM;
C: 10 nM < Ki < 100 nM;
D: 100 nM < Ki < 1000 nM
E: Ki > 1000 nM

What is claimed is:

1. A compound of Formula (I)

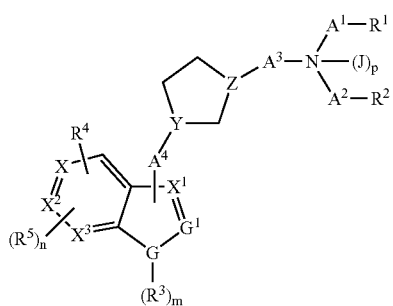

or pharmaceutically acceptable salt or solvate thereof wherein $A^1$ and $A^2$ are each independently $C_{1-4}$alkylene or a bond;
$A^3$ is a bond, $C_{1-4}$alkylene or $C_{1-4}$alkylidene;
$A^4$ is $C_{1-4}$alkylene or a bond and is attached to X, $X^1$ or $X^2$;
X, $X^1$, $X^2$ and $X^3$ are independently C or CH;
J is $C_{1-4}$alkyl;
p is 0 or 1;
$R^1$ and $R^2$ are independently H, $C_{1-3}$alkyl, $C_{3-6}$cycloalkyl, phenyl, —O-phenyl, —N(H)C(O)O—$C_{1-4}$alkyl or $C_{1-4}$alkyl-N(H)C(O)O—;

said $C_{3-6}$cycloalkyl, phenyl or O-phenyl being independently and optionally substituted with $C_{1-4}$alkyl, $C_{1-3}$alkoxy, indolyl or halo;
wherein said indolyl is optionally substituted by halo or cyano;
or are independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano;
or wherein -$A^1$-$R^1$ and -$A^2$-$R^2$ together with the nitrogen to which they are attached form pyrrolidinyl, piperidinyl, morpholino, isoindolinyl, or tetrahydroisoquinolinyl;
$R^3$ is H or $C_{1-4}$alkyl;
m is 0 or 1;
$R^4$ and $R^5$ are independently hydrogen, cyano, halo, nitro, $C_{1-3}$alkyl or $C_{1-3}$perfluoroalkyl;
wherein said $R^4$ or $R^5$ may be independently attached to $G^1$, X, $X^1$, $X^2$ or $X^3$;
n is 0 or 1;
G is N, O or S;
$G^1$ is N, C or CH;
Y is (D)H wherein D is C; and Z is (E)H wherein E is C;
provided that
  both $R^4$ and $R^5$ are not attached to the same of said $G^1$, X, $X^1$, $X^2$ or $X^3$;
  if G is O or S, then m is 0;
  if G is N, then m is 1;
  if $R_1$ is $C_{3-6}$cycloalkyl, phenyl or O-phenyl being independently and optionally substituted with $C_{1-4}$alkyl, $C_{1-3}$alkoxy, indolyl or halo; wherein said indolyl is optionally substituted by halo or cyano, then $R_2$ is H or $C_{1-3}$alkyl;
  if $R_2$ is $C_{3-6}$cycloalkyl, phenyl or O-phenyl being independently and optionally substituted with $C_{1-4}$alkyl, $C_{1-3}$alkoxy, indolyl or halo; wherein said indolyl is optionally substituted by halo or cyano, then $R_1$ is H or $C_{1-3}$alkyl;
  if $-A^1-R^1$ and $-A^2-R^2$ together with the nitrogen to which they are attached form pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, indolyl, isoindolyl, indolinyl, isoindolinyl, quinolinyl, dihydroquinolinyl, tetrahydroquinolinyl, isoquinolinyl, dihydroisoquinolinyl or tetrahydroisoquinolinyl and are optionally substituted with halo, $C_{1-4}$alkyl, $C_{1-4}$alkoxy, cyano or benzyl, then p is 0;
  if $R^1$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^1$, then $A^1$ is $C_{2-4}$alkylene;
  if $R^2$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^2$, then $A^2$ is $C_{2-4}$alkylene;
  if $R^1$ is N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^2$ is H or $C_{1-3}$alkyl;
  if $R^2$ is —N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^1$ is H or $C_{1-3}$alkyl;
  if $R^4$ or $R^5$ are attached to $G^1$, then $G^1$ is C;
  if $A^4$, $R^4$ or $R^5$ are attached to X, then X is C;
  if $A^4$, $R^4$ or $R^5$ are attached to $X^1$, then $X^1$ is C;
  if $A^4$, $R^4$ or $R^5$ are attached to $X^2$, then $X^2$ is C;
  if $R^4$ or $R^5$ are attached to $X^3$, then $X^3$ is C.

2. A compound according to claim 1 wherein p is 0.

3. A compound according to claim 1 wherein G is N and $G^1$ is CH.

4. A compound according to claim 1 wherein G is S and $G^1$ is CH.

5. A compound according to claim 1 wherein G is N and $G^1$ is N.

6. A compound according to claim 1 wherein G is S and $G^1$ is N.

7. A compound according to claim 1 wherein G is O and $G^1$ is N.

8. A compound according to claim 1 wherein $R^1$ is methyl and $R^2$ is methyl.

9. A compound according to claim 1 wherein $R^1$ is H and $R^2$ is $C_{3-6}$cycloalkyl wherein said $C_{3-6}$cycloalkyl is substituted with indolyl and wherein said indolyl is optionally substituted by halo or cyano.

10. A compound according to claim 1 wherein $A^1$ is a bond, $R^1$ is methyl, $A^2$ is a bond and $R^2$ is methyl.

11. A compound according to claim 1 wherein $R^1$ and $R^2$ are independently H, $C_{1-3}$alkyl, $C_{3-6}$cycloalkyl, phenyl, —O-phenyl, —N(H)C(O)O—$C_{1-4}$alkyl or $C_{1-4}$alkyl-N(H)C(O)O—; said $C_{3-6}$cycloalkyl, phenyl or O-phenyl being independently and optionally substituted with $C_{1-4}$alkyl, $C_{1-3}$alkoxy or halo.

12. A compound according to claim 1 wherein $R^1$ and $R^2$ are independently H, $C_{1-3}$alkyl, phenyl, said phenyl being independently and optionally substituted with $C_{1-4}$alkyl, $C_{1-3}$alkoxy or halo.

13. A compound according to claim 1 wherein $R^1$ and $R^2$ are independently H or unsubstituted $C_{1-3}$alkyl or phenyl.

14. A compound according to claim 1 wherein $R^1$ and $R^2$ are independently H or unsubstituted $C_{1-3}$alkyl or phenyl and $A^1$ and $A^2$ are independently $C_{1-4}$alkylene.

15. A compound according to claim 1 wherein $-A^1-R^1$ and $-A^2-R^2$ together with the nitrogen to which they are attached form, pyrrolidinyl, piperidinyl, morpholino, isoindolinyl, or tetrahydroisoquinolinyl and are optionally substituted with halo, $C_{1-4}$alkyl, $C_{1-4}$alkoxy, cyano or benzyl.

16. A compound according to claim 1 wherein $-A^1-R^1$ and $-A^2-R^2$ together with the nitrogen to which they are attached form unsubstituted pyrrolidinyl, piperidinyl, morpholino, or tetrahydroisoquinolinyl.

17. A compound according to claim 1 wherein $-A^1-R^1$ and $-A^2-R^2$ together with the nitrogen to which they are attached form unsubstituted pyrrolidinyl, piperidinyl, morpholino or isoindolinyl.

18. A compound according to claim 1 wherein $R^3$ is H and m is 1.

19. A compound according to claim 1 wherein n is 0.

20. A compound according to claim 1 wherein $R^4$ and $R^5$ are halo.

21. A compound according to claim 1 wherein $R^4$ is $C_{1-3}$alkyl and is attached to $G^1$.

22. A compound according to claim 1 wherein $R^4$ is $C_{1-3}$perfluoroalkyl and is attached to $G^1$.

23. A compound according to claim 1 wherein $R^4$ is hydrogen.

24. A compound according to claim 1 wherein $R^4$ is fluoro.

25. A compound according to claim 1 wherein $R^4$ is cyano.

26. A compound according to claim 1 wherein $R^4$ is cyano or fluoro.

27. A compound according to claim 1 wherein $R^4$ and $R^5$ are each fluoro.

28. A compound according to claim 1 wherein the hydrogen atom attached to D is in the trans configuration to the hydrogen atom attached to E.

29. A compound according to claim 1 wherein the hydrogen atom attached to D is in the cis configuration to the hydrogen atom attached to E.

30. A compound according to claim 1 wherein D in relation to the four moieties to which it is attached has an absolute configuration of S; E in relation to the four moieties to which it is attached has an absolute configuration of S.

31. A compound according to claim 1 wherein D in relation to the four moieties to which it is attached has an absolute configuration of S; E in relation to the four moieties to which it is attached has an absolute configuration of R.

32. A compound according to claim 1 wherein D in relation to the four moieties to which it is attached has an absolute configuration of R; E in relation to the four moieties to which it is attached has an absolute configuration of S.

33. A compound according to claim 1 wherein D in relation to the four moieties to which it is attached has an absolute configuration of R; E in relation to the four moieties to which it is attached has an absolute configuration of R.

34. A compound according to claim 1 wherein $A^3$ is a bond.

35. A compound according to claim 1 wherein $A^3$ is $C_{1-4}$alkylene.

36. A compound according to claim 1 wherein $A^3$ is $C_{1-4}$alkylidene.

37. A compound according to claim 1 wherein $A^3$ is methylene.

38. A compound according to claim 1 wherein $A^4$ is a bond.

39. A compound according to claim 1 wherein $A^4$ is methylene.

40. A compound according to claim 1 wherein $A^4$ is attached $X^1$.

41. A compound according to claim 1 wherein $A^4$ is attached X.

42. A compound according to claim 1 wherein $R^4$ is attached X.

43. A compound according to claim 1 wherein $A^1$ and $A^2$ are each independently $C_{1-4}$alkylene or a bond;

$A^3$ is a bond;

$A^4$ is a bond and is attached to $X^1$;

X and $X^1$ are each C;

$X^2$ and $X^3$ are each CH;

p is 0;

$R^1$ and $R^2$ are independently H, $C_{1-3}$alkyl, $C_{3-6}$cycloalkyl, phenyl, —O-phenyl, —N(H)C(O)O—$C_{1-4}$alkyl or $C_{1-4}$alkyl-N(H)C(O)O—;

said $C_{3-6}$cycloalkyl, phenyl or O-phenyl being independently and optionally substituted with $C_{1-4}$alkyl, $C_{1-3}$alkoxy or halo;

or are independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano;

or wherein $-A^1-R^1$ and $-A^2-R^2$ together with the nitrogen to which they are attached form pyrrolidinyl, piperidinyl, morpholino, isoindolinyl, or tetrahydroisoquinolinyl;

$R^3$ is H;

m is 1;

$R^4$ is hydrogen, cyano, halo, nitro, $C_{1-3}$alkyl or $C_{1-3}$perfluoroalkyl and is attached to X;

n is 0;

G is N;

$G^1$ is CH;

Y is (D)H wherein D is C; and

Z is (E)H wherein E is C;

provided that if $R^1$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^1$, then $A^1$ is $C_{2-4}$alkylene;

if $R^2$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^2$, then $A^2$ is $C_{2-4}$alkylene;

if $R^1$ is N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^2$ is H or $C_{1-3}$alkyl; and if $R^2$ is —N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^1$ is H or $C_{1-3}$alkyl.

44. A pharmaceutically acceptable formulation comprising a compound according to claim 1.

45. A method of treating depression, attention deficit hyperactivity disorder, obsessive-compulsive disorder, and sexual dysfunction comprising the administration to a human in need thereof an effective amount of a pharmaceutically acceptable formulation comprising a compound according to claim 1.

46. A method of treating sexual dysfunction comprising the administration to a human in need thereof an effective amount of a pharmaceutically acceptable formulation comprising a compound according to claim 1.

47. A method of treating premature ejaculation comprising the administration to a human in need thereof an effective amount of a pharmaceutically acceptable formulation comprising a compound according to claim 1.

48. A compound or pharmaceutically acceptable salt or solvate thereof selected from the group consisting of 3-(3-methylamino-cyclopentyl)-1H-indole-5-carbonitrile;
3-(3-ethylamino-cyclopentyl)-1H-indole-5-carbonitrile;
3-(3-dimethylamino-cyclopentyl)-1H-indole-5-carbonitrile;
3-[3-(ethyl-methyl-amino)-cyclopentyl]-1H-indole-5-carbonitrile;
3-(3-diethylamino-cyclopentyl)-1H-indole-5-carbonitrile;
3-(3-pyrrolidin-1-yl-cyclopentyl)-1H-indole-5-carbonitrile;
3-[3-(1,3-dihydro-isoindol-2-yl)-cyclopentyl]-1H-indole-5-carbonitrile;
3-[3-(3,4-dihydro-1H-isoquinolin-2-yl)-cyclopentyl]-1H-indole-5-carbonitrile;
3-(3-penethylamino-cyclopentyl)-1H-indole-5-carbonitrile;
3-[3-(methyl-phenethyl-amino)-cyclopentyl]-1H-indole-5-carbonitrile;
3-(3-morpholin-4-yl-cyclopentyl)-1H-indole-5-carbonitrile;
3-[3-(benzyl-methyl-amino)-cyclopentyl]-1H-indole-5-carbonitrile;
3-(3-benzylamino-cyclopentyl)-1H-indole-5-carbonitrile;
3-(3-piperidin-1-yl-cyclopentyl)-1H-indole-5-carbonitrile;
3-(3-dipropylamino-cyclopentyl)-1H-indole-5-carbonitrile;
3-(3-propylamino-cyclopentyl)-1H-indole-5-carbonitrile;
1-methyl-3-(3-methylamino-cyclopentyl)-1H-indole-5-carbonitrile;
3-(3-ethylamino-cyclopentyl)-1-methyl-1H-indole-5-carbonitrile;
3-(3-benzylamino-cyclopentyl)-1-methyl-1H-indole-5-carbonitrile;
1-methyl-3-(3-phenethylamino-cyclopentyl)-1H-indole-5-carbonitrile;
3-(3-dimethylamino-cyclopentyl)-1-methyl-1H-indole-5-carbonitrile;
3-[3-(ethyl-methyl-amino)-cyclopentyl]-1-methyl-1H-indole-5-carbonitrile;
3-(3-diethylamino-cyclopentyl)-1-methyl-1H-indole-5-carbonitrile;
1-methyl-3-(3-pyrrolidin-1-yl-cyclopentyl)-1H-indole-5-carbonitrile;
1-methyl-3-(3-piperidin-1-yl-cyclopentyl)-1H-indole-5-carbonitrile;
1-methyl-3-(3-morpholin-4-yl-cyclopentyl)-1H-indole-5-carbonitrile;
3-[3-(benzyl-methyl-amino)-cyclopentyl]-1-methyl-1H-indole-5-carbonitrile;
1-methyl-3-[3-(methyl-phenethyl-amino)-cyclopentyl]-1H-indole-5-carbonitrile;
1-methyl-3-(3-propylamino-cyclopentyl)-1H-indole-5-carbonitrile;
3-(3-dipropylamino-cyclopentyl)-1-methyl-1H-indole-5-carbonitrile;
3-[3-(benzyl-methyl-amino)-cyclopentyl]-1-ethyl-1H-indole-5-carbonitrile;
3-(3-dimethylamino-cyclopentyl)-1-ethyl-1H-indole-5-carbonitrile;
3-(5-fluoro-1H-indol-3-yl)-cyclopenty-dimethyl-amine;
ethyl-[3-(5-fluoro-1H-indol-3-yl)-cyclopentyl]-methyl-amine;
diethyl-[3-(5-fluoro-1H-indol-3-yl)-cyclopentyl]-amine;
5-fluoro-3-(3-pyrrolidin-1-yl-cyclopentyl)-1H-indole;
3-(4-fluoro-1H-indol-3-yl)-cyclopentyl-dimethyl-amine;
3-(4-bromo-1H-indol-3-yl)-cyclopentyl-dimethyl-amine;
3-(5-dhloro-1H-indol-3-yl)-cyclopentyl-dimethyl-amine;
3-(5-bromo-1H-indol-3-yl)-cyclopentyl-dimethyl-amine;
3-(5-iodo-1H-indol-3-yl)-cyclopentyl-dimethyl-amine;
3-(6-fluoro-1H-indol-3-yl)-cyclopentyl-dimethyl-amine;
3-(6-chloro-1H-indol-3-yl)-cyclopentyl-dimethyl-amine;
3-(6-bromo-1H-indol-3-yl)-cyclopentyl-dimethyl-amine;
3-(7-fluoro-1H-indol-3-yl)-cyclopentyl-dimethyl-amine;
3-(7-chloro-1H-indol-3-yl)-cyclopentyl-dimethyl-amine;
3-(7-bromo-1H-indol-3-yl)-cyclopentyl-dimethyl-amine;
(1S,3R)-3-(3-dimethylaminocyclopentyl)-1H-indole-5-carbonitrile;
(1S,3S)-3-(3-dimethylaminocyclopentyl)-1H-indole-5-carbonitrile;
(1R,3S)-3-(3-dimethylaminocyclopentyl)-1H-indole-5-carbonitrile;
(1R,3R)-3-(3-dimethylaminocyclopentyl)-1H-indole-5-carbonitrile;
(1S,3S)-3-(5-fluoro-1H-indol-3-yl)-cyclopentyl-dimethylamine;
(1R,3S)-3-(5-fluoro-1H-indol-3-yl)-cyclopentyl-dimethylamine;
(1R,3R)-3-(5-fluoro-1H-indol-3-yl)-cyclopentyl-dimethylamine;
(1S,3R)-3-(5-fluoro-1H-indol-3-yl)-cyclopentyl-dimethylamine;
(1S,3R)-3-(3-dimethylamino-cyclopentyl)-1-ethyl-1H-indole-5-carbonitrile;
(1S,3S)-3-(3-dimethylamino-cyclopentyl)-1-ethyl-1H-indole-5-carbonitrile;
(1R,3S)-3-(3-dimethylamino-cyclopentyl)-1-ethyl-1H-indole-5-carbonitrile;
(1R,3R)-3-(3-dimethylamino-cyclopentyl)-1-ethyl-1H-indole-5-carbonitrile;
(1S)-3-(3-amino-cyclopentyl)-1H-indole-5-carbonitrile; and
(3S,3'S)-bis-(3-(5-cyano-1H-indol-3-yl)cyclopentyl)amine.

* * * * *